United States Patent
Stroyer et al.

(10) Patent No.: US 10,905,667 B2
(45) Date of Patent: Feb. 2, 2021

(54) ORALLY ADMINISTRABLE MODIFIED-RELEASE PHARMACEUTICAL DOSAGE FORM

(71) Applicants: Bayer Pharma Aktiengesellschaft, Berlin (DE); Bayer Aktiengesellschaft, Leverkusen (DE)

(72) Inventors: Anke Stroyer, Berlin (DE); Carmen Lobback, Schöneiche (DE); Peter Serno, Bergisch Gladbach (DE); Philipp Rubenbauer, Bensheim (DE); Kai Lovis, Düsseldorf (DE); Heiko Schirmer, Solingen (DE); Danja Grossbach, Wuppertal (DE); Donald Bierer, Haan (DE); Britta Olenik, Bottrop (DE); Tia Jacobs, Wuppertal (DE); Julia Küsel, Bochum (DE)

(73) Assignees: BAYER PHARMA AKTIENGESELLSCHAFT, Berlin (DE); BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 16/043,567

(22) Filed: Jul. 24, 2018

(65) Prior Publication Data

US 2020/0030270 A1    Jan. 30, 2020

(51) Int. Cl.

| | | |
|---|---|---|
| *A61K 31/00* | (2006.01) | |
| *A61K 9/00* | (2006.01) | |
| *A61K 47/00* | (2006.01) | |
| *A61P 9/10* | (2006.01) | |
| *A61P 25/28* | (2006.01) | |
| *A61K 31/192* | (2006.01) | |
| *A61K 9/20* | (2006.01) | |
| *A61K 47/10* | (2017.01) | |
| *A61K 47/38* | (2006.01) | |
| *A61K 45/06* | (2006.01) | |
| *A61P 13/00* | (2006.01) | |

(52) U.S. Cl.
CPC .......... *A61K 31/192* (2013.01); *A61K 9/0004* (2013.01); *A61K 9/0053* (2013.01); *A61K 9/2086* (2013.01); *A61K 9/2095* (2013.01); *A61K 45/06* (2013.01); *A61K 47/10* (2013.01); *A61K 47/38* (2013.01); *A61P 9/10* (2018.01); *A61P 13/00* (2018.01); *A61P 25/28* (2018.01)

(58) Field of Classification Search
CPC .. A61K 31/192; A61K 9/0004; A61K 9/2086; A61K 9/2095; A61K 47/12; A61P 9/10; A61P 25/58; A61P 13/00
See application file for complete search history.

(56) References Cited

U.S. PATENT DOCUMENTS

| | | |
|---|---|---|
| 3,916,899 A | 11/1975 | Theeuwes et al. |
| 4,063,064 A | 12/1977 | Saunders et al. |
| 4,088,864 A | 5/1978 | Theeuwes et al. |
| 4,327,725 A | 5/1982 | Cortese et al. |
| 4,765,989 A | 8/1988 | Wong et al. |
| 8,796,335 B2 * | 8/2014 | Hahn ............... A61K 45/06 514/563 |
| 10,023,528 B2 | 7/2018 | Hahn et al. |
| 2003/0161882 A1 | 8/2003 | Waterman |
| 2019/0224176 A1 | 7/2019 | Kolkhof et al. |

FOREIGN PATENT DOCUMENTS

| | | |
|---|---|---|
| DE | 3417113 C2 | 2/1989 |
| EP | 0277092 B1 | 8/1988 |
| EP | 1024793 | 8/2000 |
| WO | 00/06568 A1 | 2/2000 |
| WO | 00/06569 A1 | 2/2000 |
| WO | 02/42301 A1 | 5/2002 |
| WO | 03/095451 A1 | 11/2003 |
| WO | 2006/072367 A1 | 7/2006 |
| WO | 2010/060564 A1 | 6/2010 |
| WO | 2011/147809 A1 | 12/2011 |
| WO | 2012/004258 A9 | 1/2012 |
| WO | 2012/028647 A1 | 3/2012 |
| WO | 2012/059549 A1 | 5/2012 |
| WO | 2012/139888 A1 | 10/2018 |

OTHER PUBLICATIONS

EP Patent Application 17204842.3 (filed Dec. 2017) "A process for the preparation of (3,S)-3-(4-chloro-3-2 [(S, 3 R)-2-(4-chlorophenyl)-4,4,4-trifluro-3-methylbutanoyl] amino} phenyl)-3-clopropylpropanoic acid and its crystalline form for the use as a pharmaceutical agent."
Sareen et al., "An Insight to Osmotic Drug Delivery," Current Drug Delivery, 2012; 9:285-296.
Peacock et al., "Pulmonary Circulation: Diseases and their Treatment Third Edition," 2011; 197-206.
Malaterre et al., "Oral osmotically driven systems: 30 years of development and clinical use," European Journal of Pharmaceutics and Biopharmaceutics, 2009; 73:311-323.
Hoeper et al., "Diagnosis, Assessment, and Treatment of Non-Pulmonary Arterial Hypertension Pulmonary Hypertension," J. Am. Coll. Cardiol., 2009; 54 (1):85-96.
Kumar et al., "An Overview of Recent Patents on Oral Osmotic Drug Delivery Systems," Recent Patents on Drug Delivery & Formulation, 2007; 1:236-255.
Kaushal et al., "An Update on Osmotic Drug Delivery Patents," Pharmaceutical Technology, 2003; 13(1):8-97.
Verma et al., "Formulation aspects in the development of osmotically controlled oral drug delivery systems," Journal of Controlled Release, 2002; 79:7-27.
Verma et al., "Osmotically Controlled Oral Drug Delivery," Drug Development and Industrial Pharmacy, 2000; 26:695-708.

(Continued)

*Primary Examiner* — Sikarl A Witherspoon
(74) *Attorney, Agent, or Firm* — Quarles & Brady LLP

(57) ABSTRACT

The present invention relates to orally administrable modified-release pharmaceutical dosage forms comprising sodium (3S)-3-(4-chloro-3-{[(2S,3R)-2-(4-chlorophenyl)-4,4,4-trifluoro-3-methylbutanoyl]amino}phenyl)-3-cyclopropylpropanoate and to processes for preparing the dosage forms and to their use for the treatment and/or prevention of diseases, in particular for the treatment and/or prevention of cardiac, renal and pulmonary disorders, disorders of the central nervous system, fibrotic and inflammatory disorders and metabolic disorders.

25 Claims, 3 Drawing Sheets

(56) References Cited

OTHER PUBLICATIONS

Rashmi Sareen et al: "An Insight to Osmotic Drug Delivery", Current Drug Delivery, Bd. 9, Nr. 3, Apr. 1, 2012 (Apr. 1, 2012), Seiten 285-296.
Stasch et al., "Soluble Guanylate Cyclase as an Emerging Therapeutic Target in Cardiopulmonary Disease," Circulation, May 24, 2011, pp. 2263-2273.
Evgenov at al., "NO-independerat Stimulators and Activators of Soluble Guanylate Cyciage: Discovery and Therapeutic Potential," Nature Reviews, Sep. 2008, 5, pp. 755-768.
Evgenov, Oleg V., et al. "Inhaled Agonists of Soluble Guanylate Cyclase Induce Selective Pulmonary Vasodilation." American Journal of Respiratory and Critical Care Medicine, vol. 176, 2007, pp. 1138-1145.

* cited by examiner

ORALLY ADMINISTRABLE MODIFIED-RELEASE PHARMACEUTICAL DOSAGE FORM

The present invention relates to orally administrable modified-release pharmaceutical dosage forms comprising sodium (3S)-3-(4-chloro-3-{[(2S,3R)-2-(4-chlorophenyl)-4,4,4-trifluoro-3-methylbutanoyl]amino}phenyl)-3-cyclopropylpropanoate and to processes for preparing the dosage forms and to their use for the treatment and/or prevention of diseases, in particular for the treatment and/or prevention of cardiac, renal and pulmonary disorders, disorders of the central nervous system, fibrotic and inflammatory disorders and metabolic disorders.

WO 2012/139888 discloses the compound (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (I)

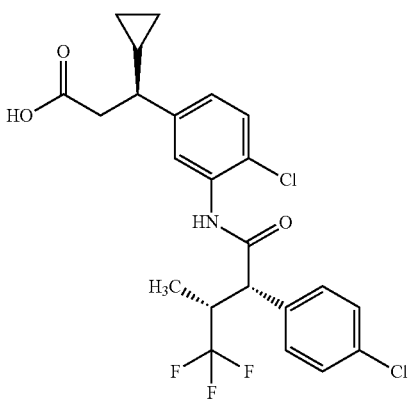

(I)

and its preparation in Example 22. The compound of the formula (I) acts as activator of soluble guanylate cyclase. The document also discloses that the chemical compounds described can generally be converted into tablets, orally administrable suspensions and orally administrable solutions. These pharmaceutical dosage forms represent exclusively rapid-release pharmaceutical compositions.

In cases of diseases which require treatment over a lengthy period, or for the long-term prophylaxis of diseases, it is desirable to keep the frequency of intake of medicaments as low as possible. This is not only more convenient for the patient, it also increases the reliability of treatment by reducing the disadvantages of irregular intake. The desired reduction in the frequency of intake, for example from administration twice a day to once a day, can be achieved by prolonging the therapeutically effective plasma levels by modified release of active ingredients from the dosage forms.

Moreover, following intake of dosage forms having a modified release of active ingredient it is possible to prevent side-effects by smoothing the plasma level time curve. By minimizing the peak-trough ratio, i.e. by avoiding high plasma active ingredient concentrations which are frequently observed after administration of rapid-release pharmaceutical forms, the occurrence of unwanted side effects correlating with the concentration peaks can be reduced. Accordingly, such a modified-release drug form should be developed. Here, an osmotic release system was chosen to ensure the required profile of a uniform, long-lasting and complete release of active ingredient over a variable, predefined time period. Compared to other delayed-release administration systems, osmotic release systems are characterized, for example, in that the release profiles can be adjusted flexibly by adjusting the thickness of the shell (Kaushal, A. M., Garg, S. *An Update on Osmotic Drug Delivery Patents. Pharmaceutical Technology.* 2003.13(1): 8-97).

Osmotic release systems are also referred to as gastrointestinal therapeutic systems (GITS) or oral osmotic systems (OROS). The long-lasting and uniform release of an active ingredient is controlled by the osmotic pressure.

Osmotic release systems can be differentiated into single-chamber systems (elementary osmotic pump) and two-chamber systems (push-pull systems).

In single-chamber systems, one or more osmotically active substances are mixed with the active ingredient and compressed. These cores are surrounded by a semipermeable membrane which has at least one orifice. This water-permeable membrane is impermeable for components of the core, but allows entry of water from outside by osmosis. The water which has penetrated in then releases, via the resulting osmotic pressure, the active ingredient in dissolved or suspended form from one or more orifices in the membrane. Overall active ingredient release and release rate can be controlled substantially via the thickness and porosity of the semipermeable membrane, the composition of the core and the number and size of the orifices.

In two-chamber systems, one chamber comprises the active ingredient, the other chamber comprises the osmotically active substance. The two chambers are separated by a flexible separating wall. This core is likewise surrounded by a semipermeable membrane which has at least one orifice on the side of the chamber containing the active ingredient.

Preferably, osmotic release systems release 80% of the active ingredient over a period of 2 to 24 hours, with preference over a period of 4 to 20 hours.

Advantages, formulation aspects, use forms and information on production processes of osmotic release systems are described inter alia in the following publications:

Kaushal, A. M., Garg, S.: "An Update on Osmotic Drug Delivery Patents", *Pharmaceutical Technology* 2003, 13, 8-97.

Kumar, P. and Mishra, B.: "An Overview of Recent Patents on Oral Osmotic Drug Delivery Systems", *Recent Patents on Drug Delivery & Formulation* 2007, 1, 236-255.

Verma, R. K., Mishra, B., Garg, S.: "Osmotically controlled oral drug delivery", *Drug Development and Industrial Pharmacy* 2000, 26, 695-708.

Verma, R. K., Krishna, D. M., Garg, S.: "Formulation aspects in the development of osmotically controlled oral drug delivery systems", *Journal of Controlled Release* 2002, 79, 7-27.

Sareen. R., Jain, N., Kumar, D.: "An Insight to Osmotic Drug Delivery", *Current Drug Delivery* 2012, 9, 285-296.

Malaterre, V., Ogorka, J., Loggia, N., Gurny, R.: "Oral osmotically driven systems: 30 years of development and clinical use", *European Journal of Pharmaceutics and Biopharmaceutics* 2009, 73, 311-323.

U.S. Pat. No. 4,327,725
U.S. Pat. No. 4,765,989
US 20030161882
EP-A 1024793

In the context of the present invention, the compound of the formula (I) should be formulated in the form of an osmotic release system to achieve long-lasting and uniform release.

The hydrophilic swellable polymer usually employed is, in particular in the case of two-chamber systems, polyethylene oxide (WO 2006/072367). Unexpectedly, the compound of the formula (I) cannot be formulated in the customary manner in the form of an osmotic release system with polyethylene oxide as hydrophilic swellable polymer. During the preparation process of the osmotic release system comprising the compound of the formula (I), melt phenomena were encountered during granulation. The resulting inefficient preparation process yielded dosage forms which did not meet the requirements and the specification of a pharmaceutical product.

When using the compound of the formula (I) and polyethylene oxide as hydrophilic swellable polymer, during dry granulation using a roller changes in the consistency of part of the granules obtained were observed. The components of the granules fused to one another giving a hard plastic-like material similar to a solidified melt, which was not suitable for further processing. The planned production process had to be abandoned. Comminution of the solidified melt by grating and sieving was possible only with high expenditure of force, material and time, which rendered the production process inefficient and unreliable with respect to a reproducible pharmaceutical quality of the product.

During further processing of the active-ingredient-comprising roller granules, which had been sieved with high expenditure, there were further disadvantageous effects during compression of the tablets. As early as in the feed funnel, "bridge formation" was observed, which means that the grains were getting caught on each other owing to the rough surface of the grains and the lack of fines. Thus, the mixture ready for compression was not flowable without additional agitation. Continuous tabletting of the granules as a mixture ready for compression was therefore not possible. Here, too, the preparation process had to be abandoned. The machine parts of the tabletting machine such as punch, template and rotary table showed significant attachment of the active-ingredient-comprising mixture for compression. The few tablets obtained showed capping tendency where the upper or the lower part of the tablet, on ejection from the tabletting press or during processing, detached partially or fully horizontally from the main part and formed a cap. Such tablets do not meet the requirements of an acceptable pharmaceutical quality and are no longer suitable for use.

When various samples of the active-ingredient-comprising powder mixture prior to granulation, of the plastic-like material prior to sieving, of the plastic-like material after comminution and sieving and of the residue on the grinding sieve were taken and analysed, significant variations in the content of the compound of the formula (I) were found. Starting with 100% of the declared active ingredient content in the active-ingredient-comprising powder mixture prior to granulation, the samples showed content values of from 107% to 120%, based on the declared active ingredient content. The consistently elevated content values are probably due to the fact that during the preparation only some of the roller granules melt and the compound of the formula (I) is present in heterogeneous form. A pharmaceutical dosage form having such deviations in the active ingredient content is unacceptable and cannot be used for further development. Preparation and marketing of such a product is impossible.

Surprisingly, by replacing the compound of the formula (I) with the sodium salt of this compound, i.e. sodium (3S)-3-(4-chloro-3-{[(2S,3R)-2-(4-chlorophenyl)-4,4,4-trifluoro-3-methylbutanoyl]amino}phenyl)-3-cyclopropylpropanoate of the formula (II)

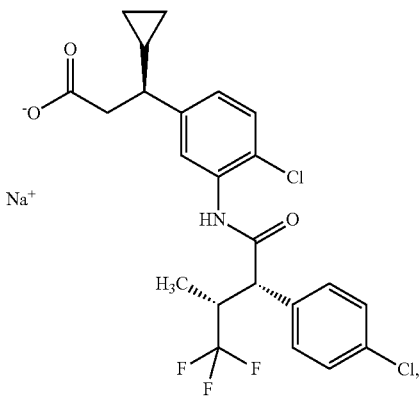

it was possible to obtain an osmotic release system which has neither the described disadvantageous properties of the osmotic release system comprising the compound of the formula (I) nor the disadvantages encountered during the described production of the osmotic release system comprising the compound of the formula (I). When the compound of the formula (II) was used, there were no melt phenomena or other disadvantageous observations made during the individual process steps. The production process could be completed without any unplanned interruptions. Content determination gave results conforming with the specifications with respect to the declared active ingredient content.

Figure 1:
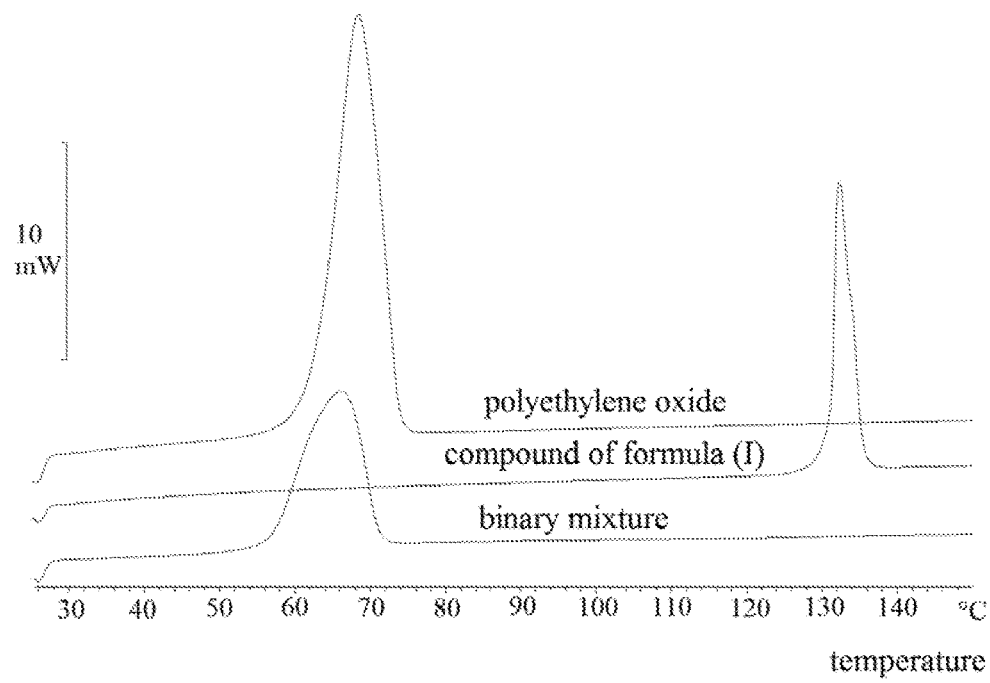
FIG. 1 shows thermograms of the compound of the formula (I), of polyethylene oxide and of a binary mixture of the compound of the formula (I) with polyethylene oxide.
Figure 2:
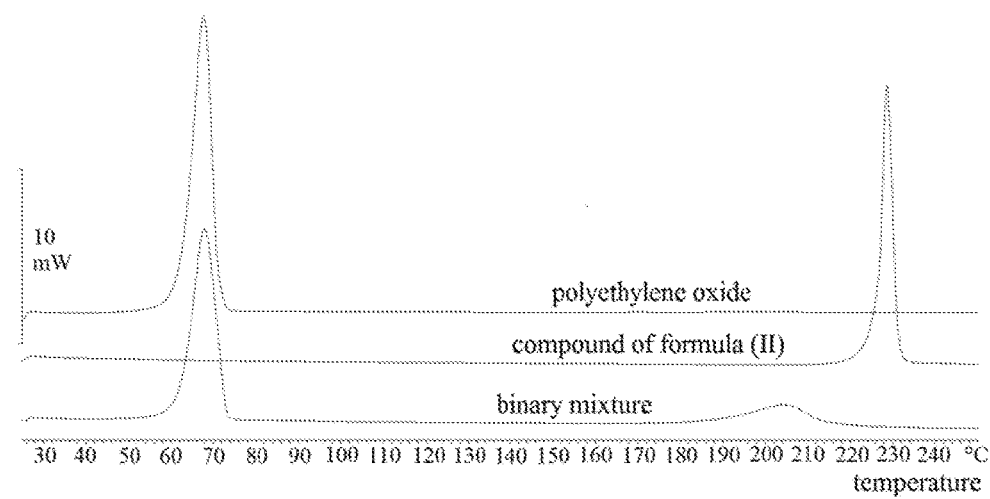
FIG. 2 shows thermograms of the compound of the formula (II), of polyethylene oxide and of a binary mixture of the compound of the formula (II) with polyethylene oxide.
Figure 3:
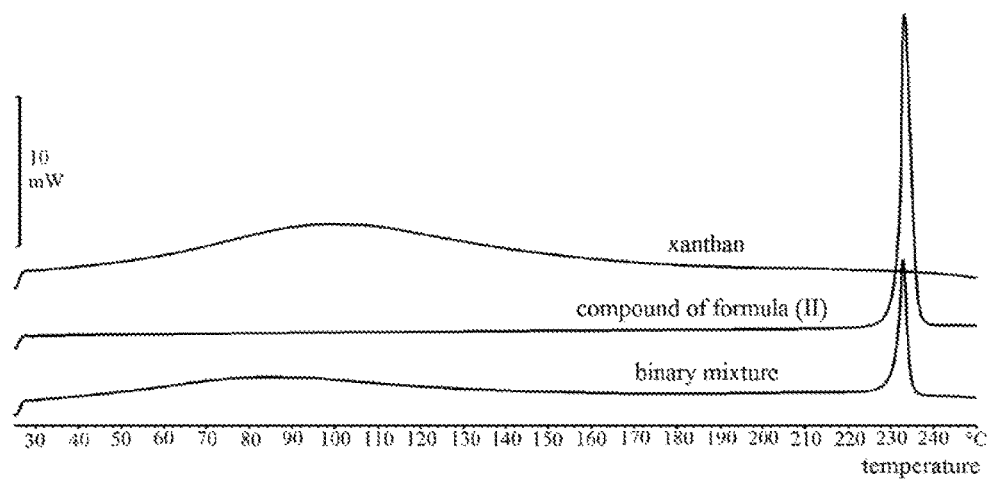
FIG. 3 shows thermograms of the compound of the formula (II), of xanthan and of a binary mixture of the compound of the formula (II) with xanthan.
Figure 4:
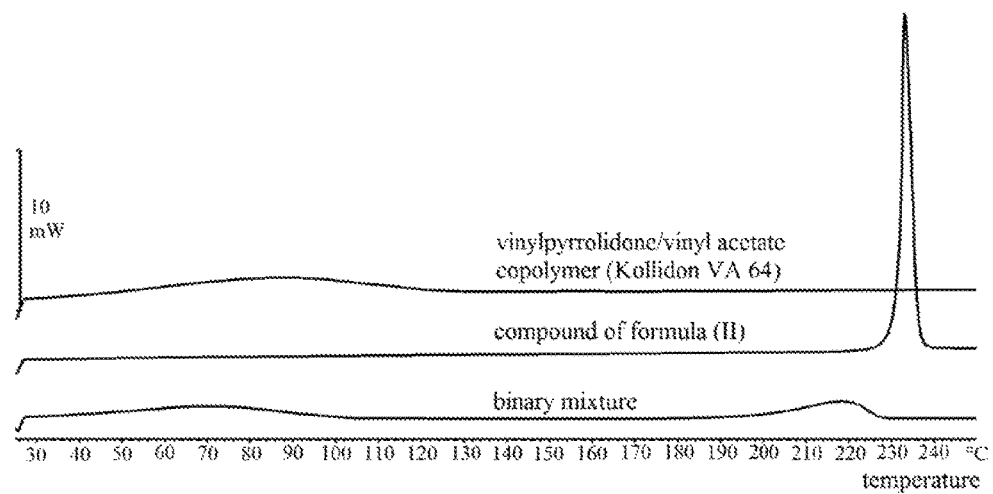
FIG. 4 shows thermograms of the compound of the formula (II), of vinylpyrrolidone/vinyl acetate copolymer and of a binary mixture of the compound of the formula (II) with vinylpyrrolidone/vinyl acetate copolymer.

The different behaviour of a mixture of the compound of the formula (I) and polyethylene oxide compared to a mixture of the compound of the formula (II) and polyethylene oxide can additionally be demonstrated by measuring the DSC (differential scanning calorimetry) thermograms of the substances in question on their own and in trituration in a ratio of 1:1 (binary mixtures). A trituration comprising equal amounts of the compound of the formula (I) and polyethylene oxide shows no melting peak which can be assigned to the compound of the formula (I) (FIG. 1). A trituration comprising equal amounts of the compound of the formula (II) and polyethylene oxide shows, in addition to the melting peak of polyethylene oxide, an additional melting peak which can be assigned to the compound of the formula (II) (FIG. 2). Binary mixtures of the compound of the formula (II) with xanthan or vinylpyrrolidone/vinyl acetate copolymer (Kollidon VA64) likewise show a melting peak which can be assigned to the compound of the formula (II) (FIGS. 3 and 4).

There have been efforts to produce a large number of other pharmaceutically acceptable salts of the compound of the formula (I). These included potassium, choline, bicarbonate, sodium carbonate, (diethylamino)ethanol, L-lysine, tris, N-methyl-D-glucamine, L-arginine, sodium bicarbonate and potassium bicarbonate salts of the compound of the formula (I). When developing a drug form, it is an important requirement that the active ingredient can be isolated reproducibly in a defined crystalline form. Compared to the amorphous form, the crystalline forms are frequently distinguished by an increased thermodynamic stability and by advantageous properties for the formulability of pharmaceutical dosage forms. Additionally, the crystalline form should have reproducible bioavailability and remain stable during the micronization process so that no conversion and recrystallization takes place.

Surprisingly, it has been found that only the sodium salt of the compound of the formula (I) could be obtained in crystalline form and that the crystalline form of the sodium salt of the compound of the formula (II) has the advantageous properties described. Hereinbelow, this crystalline form is referred to as compound of the formula (II) in crystalline form of modification 1.

All other salts of the compound of the formula (I) tested could not be obtained in crystalline form, and consequently the compound of the formula (II) was preferably used for preparing an osmotic release system.

The present invention provides a solid orally administrable modified-release pharmaceutical dosage form comprising sodium (3S)-3-(4-chloro-3-{[(2S,3R)-2-(4-chlorophenyl)-4,4,4-trifluoro-3-methylbutanoyl]amino}phenyl)-3-cyclopropylpropanoate of the formula (II), characterized in that 80% of the compound of the formula (II) are released over a period of 2 to 24, preferably 4 to 20, hours employing the apparatus 2 (paddle) USP release method.

Suitable for formulating the compounds of the formula (II) in the form of an osmotic release system are both two-chamber systems (push-pull systems) and single-chamber systems (elementary osmotic pump). Both the two-chamber system and the single-chamber system consist of a core coated with a shell and optionally a (sugar) coating. In the osmotic release systems, the compound of the formula (II) can be present either in crystalline or else in amorphous form or as a mixture comprising crystalline and amorphous portions. In the osmotic release system, the compound of the formula (II) is preferably present in crystalline form. In the osmotic release system, the compound of the formula (II) is preferably present in micronized form.

The present invention furthermore provides a solid, orally administrable modified-release pharmaceutical dosage form comprising sodium (3S)-3-(4-chloro-3-{[(2S,3R)-2-(4-chlorophenyl)-4,4,4-trifluoro-3-methylbutanoyl]amino} phenyl)-3-cyclopropylpropanoate of the formula (II),

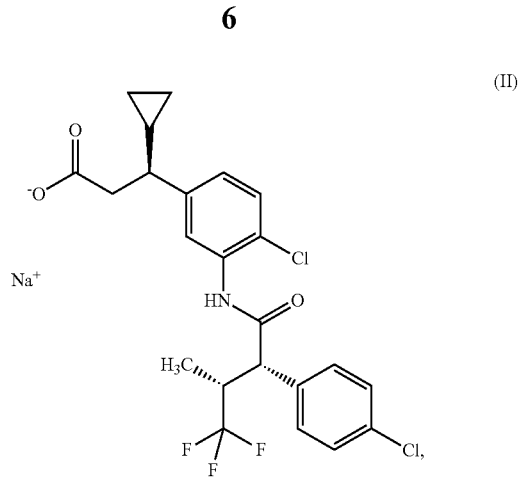

characterized in that the pharmaceutical dosage form is based on an osmotic release system.

The present invention provides a solid, orally administrable modified-release pharmaceutical dosage form comprising the compound of the formula (II), characterized in that the pharmaceutical dosage form is based on an osmotic single-chamber system.

The present invention provides a solid, orally administrable modified-release pharmaceutical dosage form comprising the compound of the formula (II), characterized in that the pharmaceutical dosage form is based on an osmotic two-chamber system.

In one embodiment, the osmotic release system consists of a core and a shell, where the shell consists of a water-permeable material impermeable for the components of the core and has at least one orifice, and where the core comprises the compound of the formula (II) and at least one hydrophilic swellable polymer.

In a further embodiment, the osmotic release system consists of a core and a shell, where the shell consists of a water-permeable material impermeable for the components of the core and has at least one orifice, and where the core comprises the compound of the formula (II) and at least one hydrophilic swellable polymer selected from a list comprising polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer and polyacrylic acids.

In a further embodiment, the osmotic release system consists of a core and a shell, where the shell consists of a water-permeable material impermeable for the components of the core and has at least one orifice, and where the core comprises the compound of the formula (II), at least one hydrophilic swellable polymer selected from a list comprising polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer and polyacrylic acids, optionally at least one pharmaceutically customary auxiliary and optionally an osmotically active additive.

In a further embodiment, the osmotic release system consists of a core and a shell, where the shell consists of a water-permeable material impermeable for the components of the core and has at least one orifice, and where the core comprises the compound of the formula (II), at least one hydrophilic swellable polymer selected from a list comprising polyethylene oxide and xanthan, optionally at least one further hydrophilic swellable polymer, optionally at least one pharmaceutically customary auxiliary and optionally an osmotically active additive.

In a further embodiment, the osmotic release system consists of a core and a shell, where the shell consists of a water-permeable material impermeable for the components of the core and has at least one orifice, and where the core comprises the compound of the formula (II), polyethylene oxide, optionally at least one further hydrophilic swellable polymer, optionally at least one pharmaceutically customary auxiliary and optionally an osmotically active additive.

In a further embodiment, the osmotic release system consists of a core and a shell, where the shell consists of a water-permeable material impermeable for the components of the core and has at least one orifice, and where the core comprises 0.5% by weight to 50% by weight of the compound of the formula (II), 40% by weight to 99.5% by weight of at least one hydrophilic swellable polymer, preferably selected from a list comprising polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer and polyacrylic acids, preferably polyethylene oxide and xanthan, particularly preferably polyethylene oxide, optionally at least one pharmaceutically customary auxiliary and optionally an osmotically active additive.

In a further embodiment, the osmotic release system consists of a core and a shell, where the shell consists of a water-permeable material impermeable for the components of the core and has at least one orifice, and where the core comprises 1% by weight to 40% by weight of the compound of the formula (II), 50% by weight to 99% by weight of at least one hydrophilic swellable polymer, preferably selected from a list comprising polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer and polyacrylic acids, preferably polyethylene oxide and xanthan, particularly preferably polyethylene oxide, optionally at least one pharmaceutically customary auxiliary and optionally an osmotically active additive.

In a further embodiment, the osmotic release system consists of a core and a shell, where the shell consists of a water-permeable material impermeable for the components of the core and has at least one orifice, and where the core comprises 2% by weight to 20% by weight of the compound of the formula (II), 60% by weight to 90% by weight of at least one hydrophilic swellable polymer, preferably selected from a list comprising polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer and polyacrylic acids, preferably polyethylene oxide and xanthan, particularly preferably polyethylene oxide, optionally at least one pharmaceutically customary auxiliary and optionally an osmotically active additive.

In a further embodiment, the osmotic release system consists of a core and a shell, where the shell consists of a water-permeable material impermeable for the components of the core and has at least one orifice, and where the core comprises 2% by weight to 10% by weight of the compound of the formula (II), 70% by weight to 85% by weight of at least one hydrophilic swellable polymer, preferably selected from a list comprising polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer and polyacrylic acids, preferably polyethylene oxide and xanthan, particularly preferably polyethylene oxide, optionally at least one pharmaceutically customary auxiliary and optionally an osmotically active additive.

In a further embodiment, the osmotic release system consists of a core and a shell, where the shell consists of a water-permeable material impermeable for the components of the core and has at least one orifice, and where the core comprises
0.5% by weight to 50% by weight of the compound of the formula (II),
10% by weight to 50% by weight of xanthan,
5% by weight to 40% by weight of a vinylpyrrolidone/vinyl acetate copolymer,
optionally at least one further hydrophilic swellable polymer, optionally at least one further pharmaceutically customary auxiliary and optionally an osmotically active additive.

The percentages by weight are in each case based on the total mass of the core.

Preferably, the osmotic single-chamber system comprises, as one of the essential components of the core, the hydrophilic water-swellable polymer xanthan. This is an anionic heteropolysaccharide which is obtainable commercially, for example under the name Rhodigel® (produced by Rhodia). It is present in an amount of from 10 to 50% by weight, preferably from 25 to 40% by weight, based on the total mass of the core components.

A further essential component of the core is the vinylpyrrolidone/vinyl acetate copolymer. This copolymer is known per se and can be produced in any desired monomer mixing ratio. For example, the commercially available Kollidon® VA64 (produced by BASF), which is preferably used, is a 60:40 copolymer. It generally has a weight average molecular weight, determined by light-scattering measurements, of about 45 000 to about 70 000. The amount of the vinylpyrrolidone/vinyl acetate copolymer in the core is 5 to 40% by weight, preferably 15 to 25% by weight, based on the total mass of the core components. Hydrophilic swellable polymers which are additionally present where appropriate in the core are, for example, hydroxypropylcellulose, hydroxypropylmethylcellulose, sodium carboxymethylcellulose, sodium carboxymethyl starch, polyacrylic acids or salts thereof.

The present invention furthermore provides a process for preparing an osmotic single-chamber system according to the invention, where the components of the core are mixed with one another, optionally subjected to wet or dry granulation and then tableted, and the resulting core is coated with the shell which is optionally additionally coated with a light-protection and/or colour coat and provided with one or more orifices suitable for the compound of the formula (II) exiting.

In a preferred embodiment of the present invention, when producing the osmotic single-chamber system the core components are subjected to wet granulation since this process step results in better wettability of the constituents of the tablet core, owing to which there is better core penetration of the ingressing gastrointestinal fluid, frequently resulting in a more rapid and more complete release of the active ingredient.

In the context of the present invention, hydrophilic swellable polymers are all pharmaceutically acceptable polymer compounds known to the person skilled in the art which swell by taking up water. Preference is given to using polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer and polyacrylic acids; preference is given to using xanthan and polyethylene oxide, very particular preference is given to using polyethylene oxide.

Osmotically active additives in the context of the present invention are, for example, all water-soluble substances acceptable for use in the pharmaceutical industry, such as, for example, the water-soluble auxiliaries mentioned in pharmacopeias, in "Hager" and "Remington Pharmaceutical Science" or other literature (Sareen. R., Jain, N., Kumar, D., *Current Drug Delivery*, 9, (2012), 285-296). It is possible in particular to use water-soluble salts of inorganic or organic acids or nonionic organic substances with high solubility in water, such as, for example, carbohydrates, especially sugars, sugar alcohols or amino acids. For example, the osmotically active additives can be selected from inorganic salts such as chlorides, sulfates, carbonates and bicarbonates of alkali metals or alkaline earth metals, such as lithium, sodium, potassium, magnesium, calcium, and phosphates, hydrogen phosphates or dihydrogen phosphates, acetates, succinates, benzoates, citrates or ascorbates thereof. It is furthermore possible to use pentoses such as arabinose, ribose or xylose, hexoses such as glucose, fructose, galactose or mannose, disaccharides such as sucrose, maltose or lactose or trisaccharides such as raffinose. The water-soluble amino acids include glycine, leucine, alanine or methionine. Preference is given to using sodium chloride.

Pharmaceutically customary auxiliaries in the context of the present invention are, for example, buffers such as sodium bicarbonate, binders such as hydroxypropylcellulose, hydroxypropylmethylcellulose, polyvinylpyrrolidone or vinylpyrrolidone/vinyl acetate copolymers (Kollidon® VA64), disintegrants such as sodium carboxymethyl starch, lubricants such as magnesium stearate, wetting agents such as sodium lauryl sulfate, flow regulators such as finely divided silica, protective colloids as described in EP-B-0277092 (p. 5, lines 10-25), plasticizers as described, for example, in EP-B-0277092 (p. 5, lines 29-32), surfactants as described, for example, in EP-B-0277092 (p. 5, lines 33-44), carrier materials as described, for example in EP-B-0277092 (p. 5, lines 45-47), and also one or more colour pigments such as, for example, iron oxide in one of the two layers for differentiation between active ingredient layer and osmosis layer. Suitable protective colloids are, for example, methylated cellulose derivatives, e.g. methylcellulose having a methoxy content of about 27.0 to 32.0% and a degree of substitution of about 1.75 to 2.1 or methylhydroxypropylcellulose having a content of about 16.0-30.0% methoxy and 4.0-32.0% hydroxypropoxy groups. Suitable plasticizers are, for example, glycerol, triethyl citrate, diethyl phthalate or diethyl sebacate. Suitable surfactants are, for example, anionic surfactants of the alkyl sulfate type, for example sodium, potassium or magnesium n-dodecyl sulfate, n-tetradecyl sulfate, n-hexadecyl sulfate or n-octadecyl sulfate, alkyl ether sulfate, for example sodium, potassium or magnesium n-dodecyloxyethyl sulfate, n-tetradecyloxyethyl sulfate, n-hexadecyloxyethyl sulfate or n-octadecyloxyethyl sulfate or alkanesulfonate, for example sodium, potassium or magnesium n-dodecanesulfonate, n-tetradecanesulfonate, n-hexadecanesulfonate or n-octadecanesulfonate. Suitable surfactants are furthermore nonionic surfactants of the fatty acid polyhydroxyalcohol ester type, such as sorbitan monolaurate, -oleate, -stearate or -palmitate, sorbitan tristearate or trioleate, polyoxyethylene adducts of fatty acid polyhydroxyalcohol esters such as polyoxyethylene sorbitan monolaurate, -oleate, -stearate, -palmitate, tristearate or trioleate, polyethylene glycol fatty esters such as polyoxyethyl stearate, polyethylene glycol 400 stearate, polyethylene glycol 2000 stearate, in particular ethylene oxide propylene oxide block polymers of the Pluronics® (BWC) or Synperonic® (ICI) type. Suitable carrier materials are, for example, lactose, sucrose, sorbitol, mannitol, starch, for example potato starch, corn starch or amylopectin, or cellulose.

Both in the single-chamber system and in the two-chamber system, the shell of the osmotic active ingredient release system consists of a water-permeable film-forming material which is impermeable for the components of the core. Such shell materials are known in principle and are described, for example, in EP1024793. Suitable for use as shell materials are cellulose derivatives, synthetic polymers and mixtures thereof.

Cellulose derivatives that may be mentioned are methylcellulose (MC), hydroxymethylpropylcellulose (HPMC), hydroxypropylcellulose (HPC), carboxymethylcellulose-sodium (Na-CMC), hydroxyethylcellulose (HEC) and mixtures thereof. It is furthermore possible to use, for example, cellulose derivatives (cellulose esters) mono- to trisubstituted by acetyl groups or mono- to disubstituted by acetyl groups and substituted by a further acyl radical different from acetyl, e.g. cellulose acetate, cellulose triacetate, cellulose acetate ethylcarbamate, cellulose acetate phthalate, cellulose acetate methylcarbamate, cellulose acetate succinate, cellulose acetate dimethylaminoacetate, cellulose acetate ethylcarbonate, cellulose acetate chloroacetate, cellulose acetate ethyloxalate, cellulose acetate methylsulfonate, cellulose acetate butylsulfonate, cellulose acetate propionate, cellulose acetate diethylaminoacetate, cellulose acetatoacetate, cellulose acetate laurate, cellulose acetate p-toluenesulfonate, cellulose acetate butyrate, and of shell materials from the group of the cellulose ethers such as ethylcellulose or other cellulose acetate derivatives and also agar acetate and amylose acetate.

Synthetic polymers that may be mentioned are polyvinylpyrrolidone (povidone, PVP), vinylpyrrolidone/vinyl acetate copolymer (copovidone), polyvinyl alcohol (PVA), polyvinyl acetate (PVAc), partially hydrolyzed polyvinyl alcohol, polyvinyl alcohol/polyethylene glycol copolymers (PVA-co-PEG) and mixtures thereof. Also suitable are Eudragit types (methacrylates), polymeric epoxides, copolymers of alkylene oxide and alkylglycidyl ethers, polyglycols, polylactic acid derivatives and other derivatives thereof. Furthermore, it is also possible to use mixtures of acrylates which are water-insoluble per se (e.g. a copolymer of ethyl acrylate and methyl methacrylate).

In the context of the present invention, preferred for use as shell materials are cellulose acetate or mixtures of cellulose acetate and polyethylene glycol.

The amounts and the constituents used for producing the shell of the osmotic drug release system influence the rate of entry of the gastrointestinal fluid in a known manner. In principle, the rate of entry of the gastrointestinal fluid decreases with an increasing amount of shell.

If required, a coat, for example a light-protection and/or colour coat, can be applied to the shell. Materials suitable for this purpose are, in principle, the same materials as those used for the shell. Particularly suitable materials are, for example, polymers such as polyvinyl alcohol, hydroxypropylcellulose and/or hydroxypropylmethylcellulose, where appropriate in combination with suitable plasticizers such as, for example, polyethylene glycol or polypropylene glycol, and pigments such as, for example, titanium dioxide or iron oxides. By way of example, mention may be made of coating with a film coat obtained by initially dissolving polyvinyl alcohol and polyethylene glycol 3350 in water at room temperature and mixing with stirring. Gradually, talc, titanium dioxide and iron oxide are added with stirring. Coating suspensions can be applied to the tablet cores using, for example, a suitable coating unit, for example a smooth coater. Alternatively, instead of coating there may be sugar coating.

The coatings used may also be finished coatings. They already comprise a mixture of auxiliaries and are dissolved in water and applied. An example which may be mentioned is Opadry II 85F230009 Orange (Colorcon PVA-based finished coating) which comprises partially hydrolyzed polyvinyl alcohol, talc, polyethylene glycol (PEG 3350), titanium dioxide, red iron oxide, yellow iron oxide and polysorbate 80 (Tween 80).

The shell and the coating/sugar coating optionally present of the osmotic drug release system of the present invention have at least one orifice or passage through which the active ingredient together with the other core constituents slowly exits. The orifice is introduced into the shell by laser drilling, mechanical drilling or, for example, by punching. One or more orifices may be present in the shell. The size of the orifice (diameter) is preferably 0.2 to 1.6 mm, particularly preferably 0.3 to 1.2 mm. The nature and the methods for producing the orifice are known per se and described, for example, in U.S. Pat. Nos. 4,063,064, 4,088,864, 3,916,899 or EP-B-0277092.

In a further embodiment, the core of the osmotic release system consists of two layers, an active ingredient layer and an osmosis layer. An osmotic two-chamber system of this type is described in detail, for example, in DE 3417113 C2, WO 2006/072367 or WO 2010/060564, the disclosures of which are incorporated herein by reference.

In a further embodiment, the osmotic release system consists of a core and a shell, where the shell consists of a water-permeable material impermeable for the components of the core and has at least one orifice, and where the core consists of an active ingredient layer and an osmosis layer.

In a further embodiment, the osmotic release system consists of a core and a shell, where the shell consists of a water-permeable material impermeable for the components of the core and has at least one orifice, and where the core consists of an active ingredient layer and an osmosis layer and the active ingredient layer comprises 1% by weight to 50% by weight of the compound of the formula (II), 20% by weight to 99% by weight of at least one hydrophilic swellable polymer, preferably selected from a list comprising polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer and polyacrylic acids, preferably polyethylene oxide and xanthan, particularly preferably polyethylene oxide, optionally at least one osmotically active additive and optionally at least one pharmaceutically customary auxiliary.

In a further embodiment, the active ingredient layer comprises 1% by weight to 45% by weight, preferably 1% by weight to 30% by weight, particularly preferably 2% by weight to 20% by weight of the compound of the formula (II), 30% by weight to 99% by weight, preferably 50% by weight to 99% by weight, particularly preferably 60% by weight to 98% by weight of at least one hydrophilic swellable polymer, optionally at least one osmotically active additive and optionally at least one pharmaceutically customary auxiliary.

In a further embodiment, the osmotic release system consists of a core and a shell, where the shell consists of a water-permeable material impermeable for the components of the core and has at least one orifice, and where the core consists of an active ingredient layer and an osmosis layer and the active ingredient layer comprises 1% by weight to 50% by weight of the compound of the formula (II), 20% by weight to 99% by weight of polyethylene oxide, preferably polyethylene oxide having a viscosity of 40 to 100 mPa·s (measured in a 5% strength aqueous solution, 25° C.), optionally at least one further hydrophilic swellable polymer, optionally at least one osmotically active additive and optionally at least one pharmaceutically customary auxiliary.

In a further embodiment, the osmotic release system consists of a core and a shell, where the shell consists of a water-permeable material impermeable for the components of the core and has at least one orifice, and where the core consists of an active ingredient layer and an osmosis layer and the active ingredient layer comprises 1% by weight to 45% by weight of the compound of the formula (II), 30% by weight to 99% by weight of polyethylene oxide, preferably polyethylene oxide having a viscosity of 40 to 100 mPa·s (measured in a 5% strength aqueous solution, 25° C.), optionally at least one further hydrophilic swellable polymer, optionally at least one osmotically active additive and optionally at least one pharmaceutically customary auxiliary.

In a further embodiment, the osmotic release system consists of a core and a shell, where the shell consists of a water-permeable material impermeable for the components of the core and has at least one orifice, and where the core consists of an active ingredient layer and an osmosis layer and the active ingredient layer comprises 1% by weight to 30% by weight of the compound of the formula (II), 50% by weight to 99% by weight of polyethylene oxide, preferably polyethylene oxide having a viscosity of 40 to 100 mPa·s (measured in a 5% strength aqueous solution, 25° C.), optionally at least one further hydrophilic swellable polymer, optionally at least one osmotically active additive and optionally at least one pharmaceutically customary auxiliary.

In a further embodiment, the osmotic release system consists of a core and a shell, where the shell consists of a water-permeable material impermeable for the components of the core and has at least one orifice, and where the core consists of an active ingredient layer and an osmosis layer and the active ingredient layer comprises 2% by weight to 20% by weight of the compound of the formula (II), 60% by weight to 98% by weight of polyethylene oxide, preferably polyethylene oxide having a viscosity of 40 to 100 mPa·s (measured in a 5% strength aqueous solution, 25° C.), optionally at least one further hydrophilic swellable polymer, optionally at least one osmotically active additive and optionally at least one pharmaceutically customary auxiliary.

The percentages by weight are in each case based on the total mass of the active ingredient layer.

The viscosity of polyethylene oxide having a viscosity of 40 to 100 mPa·s (measured in a 5% strength aqueous solution, 25° C.) is preferably measured using a suitable Brookfield viscosimeter and a suitable spindle at a suitable speed of rotation; use is made in particular of a Brookfield viscosimeter Model RVT and a spindle No. 1 at a speed of rotation of 50 rpm or using a comparable model under corresponding conditions (spindle, speed of rotation).

In a further embodiment, the osmotic release system consists of a core and a shell, where the shell consists of a water-permeable material impermeable for the components of the core and has at least one orifice, and where the core consists of one of the active ingredient layers described above and an osmosis layer, where the osmosis layer comprises 40% by weight to 90% by weight, preferably 50% by weight to 80% by weight of at least one hydrophilic swellable polymer preferably selected from a list comprising polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer and polyacrylic acids, preferably polyethylene oxide and xanthan, particularly preferably polyethylene oxide, 10% by weight to 60% by weight, preferably 20% by weight to 50% by weight of at least one osmotically active additive and optionally at least one pharmaceutically customary auxiliary.

The hydrophilic swellable polymer used in the osmosis layer is preferably polyethylene oxide. Polyethylene oxide having a viscosity of 5000 to 8000 mPa·s (measured in a 1% strength aqueous solution, 25° C.) is particularly preferred.

The viscosity of polyethylene oxide having a viscosity of 5000 to 8000 mPa·s (measured in a 1% strength aqueous solution, 25° C.) is preferably measured using a suitable Brookfield viscosimeter and a suitable spindle at a suitable speed of rotation, in particular using a Brookfield viscosimeter Model RVF and a spindle No. 2 at a speed of rotation of 2 rpm or using a comparable model under corresponding conditions (spindle, speed of rotation).

In a further embodiment, the osmotic release system consists of a core and a shell, where the shell consists of a water-permeable material impermeable for the components of the core and has at least one orifice, and where the core consists of an active ingredient layer and an osmosis layer, where the active ingredient layer comprises 0.5% by weight to 65% by weight of the compound of the formula (II), 20% by weight to 99.5% by weight of at least one hydrophilic swellable polymer, preferably selected from a list comprising polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer and polyacrylic acids, preferably polyethylene oxide and xanthan, particularly preferably polyethylene oxide, optionally at least one osmotically active additive and optionally at least one pharmaceutically customary auxiliary, and the osmosis layer comprises 40% by weight to 90% by weight of at least one hydrophilic swellable polymer, preferably selected from a list comprising polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer and polyacrylic acids, preferably polyethylene oxide and xanthan, particularly preferably polyethylene oxide, 10% by weight to 60% by weight of an osmotically active additive and optionally at least one pharmaceutically customary auxiliary.

In a further embodiment, the osmotic release system consists of a core and a shell, where the shell consists of a water-permeable material impermeable for the components of the core and has at least one orifice, and where the core consists of an active ingredient layer and an osmosis layer, where the active ingredient layer comprises 1% by weight to 50% by weight of the compound of the formula (II), 20% by weight to 99% by weight of polyethylene oxide, preferably polyethylene oxide having a viscosity of 40 to 100 mPa·s (measured in a 5% strength aqueous solution, 25° C.), optionally at least one osmotically active additive and optionally at least one pharmaceutically customary auxiliary, and the osmosis layer comprises 40% by weight to 90% by weight of polyethylene oxide, preferably polyethylene oxide having a viscosity of 5000 to 8000 mPa·s (measured in a 1% strength aqueous solution, 25° C.), 10% by weight to 60% by weight of an osmotically active additive and optionally at least one pharmaceutically customary auxiliary.

In a further embodiment, the active ingredient layer comprises 1% by weight to 45% by weight, preferably 1% by weight to 30% by weight, particularly preferably 2% by weight to 20% by weight of the compound of the formula (II), 30% by weight to 99% by weight, preferably 50% by weight to 99% by weight, particularly preferably 60% by weight to 98% by weight of polyethylene oxide having a viscosity of 40 to 100 mPa·s (measured in a 5% strength aqueous solution, 25° C.), optionally at least one osmotically active additive and optionally at least one pharmaceutically customary auxiliary, and the osmosis layer comprises 40% by weight to 90% by weight, preferably 50% by weight to 80% by weight of polyethylene oxide having a viscosity of 5000 to 8000 mPa·s (measured in a 1% strength aqueous solution, 25° C.), 10% by weight to 60% by weight, preferably 20% by weight to 50% by weight of at least one osmotically active additive and optionally at least one pharmaceutically customary auxiliary.

In a further embodiment, the osmotic release system consists of a core and a shell, where the shell consists of a water-permeable material impermeable for the components of the core and has at least one orifice, and where the core consists of an active ingredient layer and an osmosis layer, where the active ingredient layer comprises 2% by weight to 20% by weight of the compound of the formula (II), 60% by weight to 98% by weight of polyethylene oxide having a viscosity of 40 to 100 mPa·s (measured in a 5% strength aqueous solution, 25° C.), optionally at least one osmotically active additive and optionally at least one pharmaceutically customary auxiliary, and the osmosis layer comprises 50% by weight to 80% by weight of polyethylene oxide having a viscosity of 5000 to 8000 mPa·s (measured in a 1% strength aqueous solution, 25° C.), 20% by weight to 50% by weight of an osmotically active additive and optionally at least one pharmaceutically customary auxiliary.

In a further embodiment, the osmotic release system consists of one of the osmotic release systems described above, where the shell consists of cellulose acetate or a mixture of cellulose acetate and polyethylene glycol.

Preferred for use as hydrophilic swellable polymer in the embodiments described are polyethylene oxide, xanthan, hydroxypropylcellulose, hydroxypropylmethylcellulose, sodium carboxymethylcellulose, sodium carboxymethyl starch, vinylpyrrolidone/vinyl acetate copolymer, polyacrylic acids and salts thereof, particularly preferably polyethylene oxide.

Preferred for use as osmotically active additive in the embodiments described is at least one water-soluble salt of inorganic or organic acids, particularly preferably sodium chloride.

Preferred for use as pharmaceutically customary auxiliaries in the embodiments described are binders, for example hydroxypropylcellulose, lubricants, for example magnesium stearate, flow regulators, for example finely divided silica, and colour pigments, for example iron oxide.

To prepare the osmotic two-chamber system, it is possible, for example, to mix the components of the active ingredient layer and to subject them to wet or dry, preferably dry, granulation, to mix and granulate the components of the osmosis layer and then to compress both sets of granules on a bilayer tablet press to give a bilayer tablet. The resulting inner core is then coated with a shell. The shell is, on the active ingredient side, provided with one or more orifices. Alternatively, the provision of the one or more orifices in this process step may be dispensed with. In this case, only after the coating with one or more further mantle coatings has been carried out, both sides of the tablet are each provided with an orifice extending in each case from the outside to the inner core, i.e. stretching across the mantle coatings and the shell.

Preferably, both the components of the active ingredient layer and the components of the osmosis layer are each subjected to granulation, in particular by means of roller granulation, in the production of the osmotic two-chamber system.

Preference is given according to the invention, because of the physicochemical properties of the active ingredient, to osmotic two-chamber systems (push-pull systems) in which the active ingredient layer and the osmosis layer are separated, by way of example and with preference formulated as a bilayer tablet. Here, the advantages compared to osmotic single-chamber systems are the more uniform release rate over a longer period of time, and also the possibility to reduce the systemically required excess of active ingredient.

The present invention furthermore provides the compound sodium (3S)-3-(4-chloro-3-{[(2S,3R)-2-(4-chlorophenyl)-4,4,4-trifluoro-3-methylbutanoyl]amino}phenyl)-3-cyclopropylpropanoate of the formula (II)

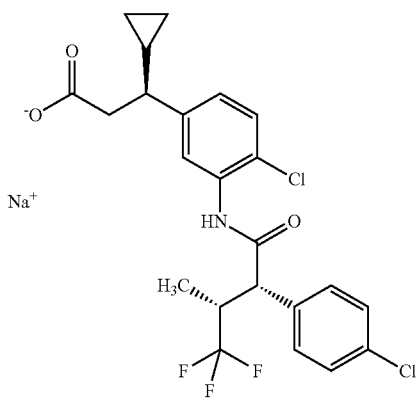

Also provided is the compound of the formula (II) in crystalline form of modification 1, characterized in that the X-ray diffractogram of the compound has peak maxima of the 2 theta angle at 8.1, 17.2, 18.8, 22.3 and 22.6°.

Also provided is the compound of the formula (II) in crystalline form of modification 1, characterized in that the X-ray diffractogram of the compound has peak maxima of the 2 theta angle at 6.5, 8.1, 17.2, 18.8, 22.3, 22.6 and 25.5°.

Also provided is the compound of the formula (II) in crystalline form of modification 1, characterized in that the X-ray diffractogram of the compound has peak maxima of the 2 theta angle at 6.5, 8.1, 16.4, 17.2, 18.0, 18.8, 19.4, 22.3, 22.6 and 25.5°.

Also provided is the compound of the formula (II) in crystalline form of modification 1, characterized in that the IR spectrum of the compound has band maxima at 3381, 1691 and 1565 cm$^{-1}$.

Also provided is the compound of the formula (II) in crystalline form of modification 1, characterized in that the IR spectrum of the compound has band maxima at 3381, 1691, 1565, 1524 and 1419 cm$^{-1}$.

Also provided is the compound of the formula (II) in crystalline form of modification 1, characterized in that the IR spectrum of the compound has band maxima at 3381, 3066, 1691, 1565, 1524, 1419 and 1101 cm$^{-1}$.

Also provided is the compound of the formula (II) in crystalline form of modification 1, characterized in that the IR spectrum of the compound has band maxima at 3381, 3066, 2975, 1691, 1565, 1524, 1419, 1135, 1101 and 817 cm$^{-1}$.

The compound of the formula (II) in crystalline modification 1 can be prepared from the compound of the formula (I). The preparation of the compound of the formula (I) in amorphous form is disclosed in WO 2012/139888 as Example 22. The preparation of the compound of the formula (I) in crystalline form is disclosed in EP17204842.3. Both the compound of the formula (I) in amorphous form and the compound of the formula in crystalline form are equally suitable for preparing the compound of the formula (II) in crystalline modification 1 in the processes described below.

When preparing the compound of the formula (II) from the compound of the formula (I), there is the risk that the compound of the formula (I) epimerizes to (3S)-3-(4-chloro-3-{[(2R,3R)-2-(4-chlorophenyl)-4,4,4-trifluoro-3-methylbutanoyl]amino}phenyl)-3-cyclopropylpropanoic acid of the formula (III),

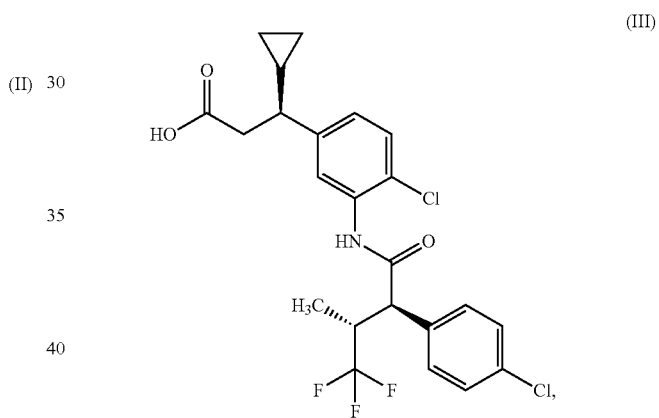

or that the compound of the formula (II) epimerizes to sodium (3S)-3-(4-chloro-3-{[(2R,3R)-2-(4-chlorophenyl)-4,4,4-trifluoro-3-methylbutanoyl]amino}phenyl)-3-cyclopropylpropanoate of the formula (IV),

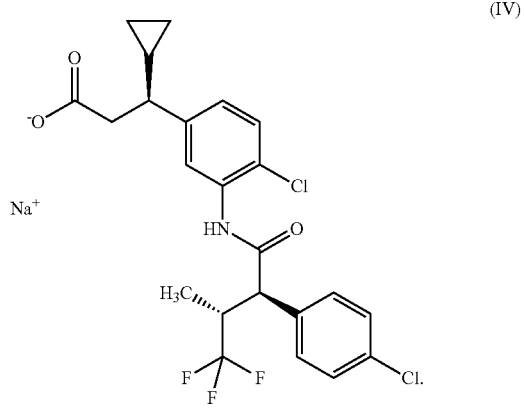

Thus, for example, there is significant epimerization during the preparation of the compound of the formula (II) with aqueous sodium hydroxide solution or when the solvent used is methanol or ethanol. As a consequence, relevant amounts of the compounds of the formulae (III) and (IV) are produced in such reactions, thus reducing the yield of the desired compound of the formula (II). Accordingly, epimerization should be avoided. Surprisingly, in the preparation processes described below, there was little of this side reaction.

To prepare the compound of the formula (II) in crystalline modification 1, the compound of the formula (I) is, preferably under protective gas atmosphere, for example under nitrogen atmosphere, dissolved in a polar aprotic solvent. Suitable for use as polar aprotic solvent are, for example, acetonitrile, toluene, methyl tert-butyl ether (MTBE) or tetrahydrofuran (THF); preference is given to using acetonitrile. Subsequently sodium hydroxide is used, preferably in solid form. The mixture is stirred, preferably for several hours. After filtration, the solid obtained is washed with a polar aprotic solvent and dried.

In particular the choice of solvent, the amount of sodium hydroxide employed and the use of sodium hydroxide in solid form lead to a reduction of the unwanted epimerization of the compound of the formula (I) during the synthesis.

In particular for the production of relatively large amounts (kilogram scale) of the compound of the formula (II), there is the possibility that part of the solid sodium hydroxide is not converted during the reaction and, after filtration, remains in the solid obtained. Accordingly, an alternative preparation process (Preparation Process 2) was developed.

In an alternative preparation method, the compound of the formula (I) is, preferably under protective gas atmosphere, for example under nitrogen atmosphere, dissolved in a polar aprotic solvent and preferably filtered. Suitable for use as polar aprotic solvent are, for example, acetonitrile, toluene, methyl tert-butyl ether (MTBE) or tetrahydrofuran (THF); preference is given to using acetonitrile. The solution is cooled and, preferably at a temperature of −20° C. to 50° C., particularly preferably −10° C. to 10° C., very particularly preferably 0° C., a sterically demanding sodium alkoxide, for example sodium tert-butoxide or sodium 2-methylbut-2-oxide, dissolved in a suitable polar aprotic solvent is added. The sterically demanding sodium alkoxide is preferably employed in an amount of 0.7 to 1.0 molar equivalents, particularly preferably 0.9 to 1.0 molar equivalents and very particularly preferably 0.98 molar equivalents, based on the compound of the formula (I). Suitable for use as polar aprotic solvent are, for example, acetonitrile, toluene, methyl tert-butyl ether (MTBE), 2-methyltetrahydrofuran or tetrahydrofuran (THF); preference is given to using THF. During the addition of the sterically demanding sodium alkoxide, seed crystals of the compound of the formula (II) in crystalline modification 1 may be added. This results in a more efficient precipitation and a higher yield. The seed crystals can be prepared, for example, by Preparation Process 1. The mixture is stirred at −20° C. to 20° C., preferably −5° C. to 5° C., particularly preferably 0° C., preferably for several hours. After filtration, the solid obtained is washed with a polar aprotic solvent and dried.

Surprisingly, the amount of base, in relation to the amount of the compound of the formula (I) employed, has a strong effect on the extent of epimerization. 0.7 to 1.0 molar equivalents, preferably 0.9 to 1.0 molar equivalents and particularly preferably 0.98 molar equivalents of base, relative to the compound of the formula (I), are advantageous.

Alternatively, the compound of the formula (II) in crystalline modification 1 can be prepared by dissolving the amorphous form of the compound of the formula (II) or another modification of the compound of the formula (II) in a polar solvent, for example tetrahydrofuran, isopropanol or methanol, and subsequent crystallization.

The present invention provides the preparation of the compound of the formula (II) in crystalline modification 1, characterized in that the compound of the formula (I) is dissolved in a polar aprotic solvent, a base selected from a list comprising sodium hydroxide or a sterically demanding sodium alkoxide is added and the precipitated solid is, after stirring, isolated and dried.

The present invention provides the preparation of the compound of the formula (II) in crystalline modification 1, characterized in that the compound of the formula (I) is dissolved in a polar aprotic solvent, preferably acetonitrile, toluene, methyl tert-butyl ether (MTBE) or tetrahydrofuran (THF), particularly preferably acetonitrile, a base selected from a list comprising sodium hydroxide or a sterically demanding sodium alkoxide is added and the precipitated solid is, after stirring, isolated and dried.

If the base used is sodium hydroxide, preference is given to using sodium hydroxide in solid form.

The present invention provides the preparation of the compound of the formula (II) in crystalline modification 1, characterized in that the compound of the formula (I) is dissolved in acetonitrile, sodium hydroxide in solid form is added and the precipitated solid is, after stirring, isolated and dried.

The base is preferably employed in an amount of 0.7 to 1.0 molar equivalents, particularly preferably 0.9 to 1.0 molar equivalents and very particularly preferably 0.98 molar equivalents, based on the compound of the formula (I).

Sterically demanding sodium alkoxides include all suitable sodium alkoxides known to the person skilled in the art whose chemical structure is more complex than that of sodium methoxide or sodium ethoxide. Preferred sterically demanding sodium alkoxides are, for example, sodium tert-butoxide or sodium 2-methylbut-2-oxide.

The present invention provides the preparation of the compound of the formula (II) in crystalline modification 1, characterized in that the compound of the formula (I) is dissolved in a polar aprotic solvent, preferably acetonitrile, toluene, methyl tert-butyl ether (MTBE) or tetrahydrofuran (THF), particularly preferably acetonitrile, a base selected from a list comprising sodium hydroxide, sodium tert-butoxide and sodium 2-methylbut-2-oxide is added and the precipitated solid is, after stirring, isolated and dried.

The present invention provides the preparation of the compound of the formula (II) in crystalline modification 1, characterized in that the compound of the formula (I) is dissolved in acetonitrile, sodium tert-butoxide is added and the precipitated solid is, after stirring, isolated and dried.

The present invention provides the preparation of the compound of the formula (II) in crystalline modification 1, characterized in that the compound of the formula (I) is dissolved in acetonitrile, sodium 2-methylbut-2-oxide is added and the precipitated solid is, after stirring, isolated and dried.

The base is preferably employed in an amount of 0.7 to 1.0 molar equivalents, particularly preferably 0.9 to 1.0 molar equivalents and very particularly preferably 0.98 molar equivalents, based on the compound of the formula (I).

The present invention provides the preparation of the compound of the formula (II) in crystalline modification 1, characterized in that the compound of the formula (I) is dissolved in acetonitrile, sodium tert-butoxide is added in an amount of 0.7 to 1.0 molar equivalents, particularly preferably 0.9 to 1.0 molar equivalents and very particularly preferably 0.98 molar equivalents, based on the compound of the formula (I), and the precipitated solid is, after stirring, isolated and dried.

The present invention provides the preparation of the compound of the formula (II) in crystalline modification 1, characterized in that the compound of the formula (I) is dissolved in acetonitrile, sodium 2-methylbut-2-oxide is added in an amount of 0.7 to 1.0 molar equivalents, particularly preferably 0.9 to 1.0 molar equivalents and very particularly preferably 0.98 molar equivalents, based on the compound of the formula (I), and the precipitated solid is, after stirring, isolated and dried.

Addition of the base and subsequent stirring are, independently of one another, carried out at a temperature of −20° C. to 50° C., preferably −20° C. to 20° C., particularly preferably −10° C. to 10° C., very particularly preferably 0° C.

Optionally, seed crystals of the compound of the formula (II) in crystalline modification 1 may be added during the reaction.

The compound of the formula (II) according to the invention and the dosage forms according to the invention have valuable pharmacological properties and can be used for treatment and/or prevention of disorders in humans and animals.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The compound of the formula (II) according to the invention and the dosage forms according to the invention lead to vascular relaxation, inhibition of platelet aggregation and lowering of blood pressure, and they also increase coronary blood flow and microcirculation. These effects are mediated by a direct, haem-independent activation of soluble guanylate cyclase and a rise of intracellular cGMP levels.

The compound of the formula (II) according to the invention and the dosage forms according to the invention are especially suitable for the treatment and/or prevention of renal and cardiorenal disorders, in particular chronic kidney disease (CKD) and diabetic kidney disease (DKD), cardiac and cardiovascular disorders, in particular heart failure (HFpEF and HFrEF), myocardial infarction, angina pectoris, cardiomyopathies, hypertension and arteriosclerosis, pulmonary and cardiopulmonary disorders, in particular pulmonary hypertension (PH), disorders of the central nervous system, in particular dementia, bone disorders, in particular osteogenesis imperfecta, thromboembolic disorders, muscular dystrophies, ischaemias, vascular disorders, impaired microcirculation, fibrotic disorders, in particular systemic sclerosis, in particular age-related macular degeneration, inflammatory disorders, and metabolic disorders, in particular metabolic syndrome, dyslipidaemia and diabetes.

The compound of the formula (II) according to the invention and the dosage forms according to the invention can be used for the treatment and/or prevention of cardiac, cardiovascular and cardiopulmonary disorders such as, for example high blood pressure (hypertension), heart failure, coronary heart disease, stable and unstable angina pectoris, pulmonary arterial hypertension (PAH) and secondary forms of pulmonary hypertension (PH), chronic thromboembolic pulmonary hypertension (CTEPH), renal hypertension, disorders of peripheral and cardial vessels, arrhythmias, atrial and ventricular arrhythmias and impaired conduction such as, for example, grade I-III atrioventricular blocks, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV nodes reentry tachycardia, Wolff-Parkinson-White syndrome, acute coronary syndrome (ACS), autoimmune heart disorders (pericarditis, endocarditis, valvolitis, aortitis, cardiomyopathies), boxer cardiomyopathy, aneurysms, shock such as cardiogenic shock, septic shock and anaphylactic shock.

The compound of the formula (II) according to the invention and the dosage forms according to the invention can be used for the treatment and/or prevention of thromboembolic disorders and ischaemias such as myocardial ischaemia, myocardial infarction, stroke, cardial hypertrophy, transistory and ischaemic attacks, preeclampsia, inflammatory cardiovascular disorders, spasms of the coronary arteries and the peripheral arteries, formation of oedemas such as, for example, pulmonary oedema, brain oedema, renal oedema or heart failure-induced oedema, impaired peripheral perfusion, reperfusion damage, arterial and venous thromboses, microalbuminuria, heart failure, endothelial dysfunction, micro- and macrovascular damage (vasculitis), and also for preventing restenoses for example after thrombolysis therapies, percutaneous transluminal angioplasties (PTA), percutaneous transluminal coronary angioplasties (PTCA), heart transplants, bypass operations and micro- and macrovascular damage (vasculitis), increased level of fibrinogen and of low-density LDL and increased concentrations of plasminogen activator inhibitor 1 (PAI-1), and for the treatment and/or prophylaxis of erectile dysfunction and female sexual dysfunction.

In the context of the present invention, the term "pulmonary hypertension" includes both primary and secondary sub-forms thereof as defined according to the Dana Point classification in accordance with their respective etiology [see D. Montana and G. Simonneau, in: A. J. Peacock et al. (Eds.), *Pulmonary Circulation. Diseases and their treatment*, 3$^{rd}$ edition, Hodder Arnold Publ., 2011, pp. 197-206; M. M. Hoeper et al., *J. Am. Coll. Cardiol.*, 2009, 54 (1), p 85-p 96]. These include in particular in Group 1 pulmonary arterial hypertension (PAH), which includes inter alia the idiopathic and the familiar forms (IPAH and FPAH, respectively), acute pulmonary hypertension, in particular the acute respiratory distress syndrome (ARDS), acute lung injury (ALI) and infant respiratory distress syndrome (IRDS). Furthermore, PAH also embraces persistent pulmonary hypertension of the newborn and the associated pulmonary arterial hypertension (APAH) associated with collagenoses, congenital systemic pulmonary shunt lesions, portal hypertension, HIV infections, the intake of certain drugs and medicaments (for example of appetite suppressants), with disorders having a significant venous/capillary component such as pulmonary venoocclusive disorder and pulmonary capillary haemangiomatosis, or with other disorders such as disorders of the thyroid, glycogen storage diseases, Gaucher disease, hereditary teleangiectasia, haemoglobinopathies, myeloproliferative disorders and splenectomy. Group 2 of the Dana Point classification comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (ILD), pulmonary fibrosis (IPF), and/or hypoxaemia, sleep apnoea syndrome, alveolar hypoventilation, chronic high-altitude sickness, hereditary deformities. Group 4 includes PH patients having chronic thrombotic and/or embolic disorders, for example in the case of thromboembolic obstruction of proximal and distal pulmonary arteries (CTEPH) or non-thrombotic embolisms (e.g. as a result of tumour disorders, parasites, foreign bodies). Less common forms of pulmonary hypertension, such as in patients suffering from sarcoidosis, histiocytosis X or lymphangiomatosis, are summarized in group 5.

In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilatative cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure, heart failure with reduced ejection fraction (HFrEF), heart failure with preserved ejection fraction (HFpEF).

The compound of the formula (II) according to the invention and the dosage forms according to the invention are also suitable for the treatment and/or prevention of metabolic disorders. In the context of the present invention, metabolic disorders are, for example, disorders of glucose metabolism and disorders and complications associated with impaired glucose metabolism. Disorders of glucose metabolism are, for example, Diabetes mellitus (Type 1 or Type 2), insulin resistance, impaired glucose tolerance, hyperglycaemia, hypoglycaemia, hyperinsulinaemia or hypoinsulinaemia. Disorders associated with impaired glucose metabolism are, for example, micro- and macroangiopathies, diabetic retinopathies, diabetic neuropathies, diabetic nephropathies, delayed/impaired wound healing, diabetic foot, tissue ischaemias, ulcers on the extremities, gangrene, metabolic acidosis, ketosis, dyslipidaemias, myocardial infarction, acute coronary syndrome, stable or unstable angina pectoris, cardiomyopathies, heart failure, cardiac arrhythmias, vascular restenosis, peripheral arterial occlusive disease, obesity, syndrome X, impaired fat metabolism, arteriosclerosis or high blood pressure. The compound of the formula (II) according to the invention and the dosage forms according to the invention are also suitable for maintaining, improving and restoring the functions of cells of the pancreas, in particular for maintaining, improving and restoring the number and size of the 3 cells of the pancreas.

In the context of the present invention, metabolic disorders also include disorders of fat metabolism such as, for example, impaired lipid metabolism, hypolipoproteinaemias, dyslipidaemias, hypertriglyceridaemias, hyperlipidaemias, combined hyperlipidaemias, hypercholesterolaemias, abetalipoproteinaemia, sitosterolaemia, xanthomatosis, Tangier disease, adiposity, obesity, arteriosclerosis and metabolic syndrome. The compound of the formula (II) according to the invention and the dosage forms according to the invention are also suitable for the treatment and/or prevention of cardiovascular disorders associated with a metabolic disorder.

The compound of the formula (II) according to the invention and the dosage forms according to the invention are also suitable for the treatment and/or prevention of muscular or neuromuscular disorders. The expression "muscular or neuromuscular disorders" relates to a medical condition affecting the muscles and/or their direct control of the nervous system. They may be acquired or of genetic origin. Muscular or neuromuscular disorders are in particular Duchenne muscular dystrophy (DMD), Becker muscular dystrophy (BMD), congenital muscular dystrophy, Miyoshi myopathy, Emery-Dreifuss muscular dystrophy, facioscapulohumeral muscular dystrophy, limb-girdle muscular dystrophy, myotonic muscular dystrophy, oculopharyngeal muscular dystrophy, myasthenia gravis, Lambert-Eaton myasthenic syndrome and Charcot-Marie-Tooth disease.

Furthermore, the compound of the formula (II) according to the invention and the dosage forms according to the invention may be employed for the treatment and/or prevention of primary and secondary Raynaud phenomena, microcirculation impairments, claudication, hearing difficulties, tinnitus, peripheral and autonomous neuropathies, diabetic microangiopathies, diabetic retinopathy, CREST syndrome, erythematosis, onychomycosis and rheumatic disorders.

The compound of the formula (II) according to the invention and the dosage forms according to the invention can additionally be employed for the treatment and/or prevention of ischaemia- and/or reperfusion-related damage to organs or tissues and as additive for perfusion and preservation solutions for organs, organ parts, tissues or tissue parts of human or animal origin, in particular for surgical interventions or in the field of transplantation medicine.

The compound of the formula (II) according to the invention and the dosage forms according to the invention are also suitable for treatment and/or prevention of renal disorders, in particular renal insufficiency and kidney failure. In the context of the present invention, the terms "renal insufficiency" and "kidney failure" encompass both acute and chronic manifestations thereof (chronic kidney disease; CKD) and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, diabetic kidney disease (DKD), pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also encompasses the use of the dosage forms according to the invention for treatment and/or prevention of sequelae of renal insufficiency, for example hypertension, pulmonary oedema, heart failure, uraemia, anaemia, electrolyte disturbances (for example hyperkalaemia, hyponatraemia) and disturbances in bone and carbohydrate metabolism.

In addition, the compound of the formula (II) according to the invention and the dosage forms according to the invention are suitable for the treatment and/or prevention of disorders of the urogenital system, for example benign prostate syndrome (BPS), benign prostate hyperplasia (BPH), benign prostate enlargement (BPE), bladder outlet obstruction (BOO), lower urinary tract syndromes (LUTS), interstitial cystitis, neurogenic overactive bladder (OAB), incontinence, for example mixed urinary incontinence, urge urinary incontinence, stress urinary incontinence or overflow urinary incontinence (MUI, UUI, SUI, OUI), pelvic pain, erectile dysfunction, female sexual dysfunction, vaginal atrophy, dyspareunia or atrophic vaginitis.

The compound of the formula (II) according to the invention and the dosage forms according to the invention are also suitable for treatment and/or prevention of asthmatic disorders, chronic-obstructive pulmonary diseases (COPD), acute respiratory distress syndrome (ARDS) and acute lung injury (ALI), alpha-1 antitrypsin deficiency (AATD), pulmonary fibrosis, pulmonary emphysema (for example pulmonary emphysema induced by cigarette smoke), pulmonary venous hypertension, interstitial lung disorder, sleep apnoea, alveolar hypoventilation impairments, chronic exposition to high altitudes, neonatal lung disorder, alveolar capillary dysplasia, sickle cell anaemia, impaired coagulation, chronic thromboembolism, tumour-associated pulmonary embolism, disorders of the connective tissue, lupus, schistosomiasis, sarcoidosis, chronic bronchitis, capillary pulmonary haemangiomatosis; histiocytosis X, lymphangiomatosis and compressed lung vessels owing to adenopathy, fibrosing mediastinitis and cystic fibrosis (CF).

The compound of the formula (II) according to the invention described in the present invention and the dosage forms according to the invention are also active compounds and dosage forms for the control of diseases in the central nervous system which are characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, dementia, vascular dementia, mixed forms of dementia, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff's psychosis, Binswanger dementia (subcortical arteriosclerotic encephalopathy), cerebral autosomal-dominant arteriopathy with subcortical infarcts and leukoencephalopathy (iCADASIL or CADASIL syndrome), asymptomatic neurocognitive impairment (ANI), multiple sclerosis (MS) (including the clinically isolated syndrome (CIS), relapsing-remitting MS (RRMS), primary progressive MS (PPMS) and secondary progressive MS (SPMS), multisystem atrophy (MSA), Parkinson's disease, Parkinson plus, progressive supranuclear palsy (PSP, Steele-Richardson-Olszewski syndrome), attention deficit syndrome (ADS) and attention deficit hyperactivity disorder (ADHS). They are also suitable for treatment and/or prevention of central nervous system disorders such as states of anxiety, tension and depression, CNS-related sexual dysfunctions and sleep disturbances, and for controlling pathological disturbances of the intake of food, stimulants and addictive substances. They are also suitable for the treatment and/or prevention of injuries, for example traumatic brain injury (TBI) including, for example, concussion and traumatic encephalopathies (CTE), or non-traumatic strokes (including ischaemic strokes, aneurysms or hypoxias), brain damage, cognitive impairments, brain injuries, neurodegenerative disorders or neuropathic pain. They are also suitable for the treatment and/or prevention of dystonias, for example general, focal, segmental, vegetative, acute dystonic reactions and genetic/primary dystonias and dyskinesias, including acute, chronic/tardive and non-motoric and levodopa-induced dyskinesias (LID). They are also suitable for the treatment and/or prevention of disorders characterized by reduced synaptic plasticity and synaptic processes, for example fragile X syndrome, Rett syndrome, Williams syndrome, Renpenning syndrome, disorders of the autism spectrum including autism, Asperger syndrome or far-reaching development disorders. They are also suitable for the treatment and/or prevention of mental, affective or psychological disorders, for example bipolar disorder, schizophrenia, general psychosis, drug-induced psychosis, paranoia, schizoaffective disorder, obsessive-compulsive disorder (OCD), depressive disorders, anxiety disorders, panic disorders or posttraumatic stress disorder (PTSD). Furthermore, the compound of the formula (II) according to the invention and the dosage forms according to the invention are also suitable for controlling cerebral blood flow and are thus effective agents for controlling migraines. They are also suitable for the prophylaxis and control of sequelae of cerebral infarct (Apoplexia cerebri) such as stroke, cerebral ischaemias and craniocerebral trauma. The dosage forms according to the invention can likewise be employed for controlling states of pain.

In addition, the compound of the formula (II) according to the invention and the dosage forms according to the invention have anti-inflammatory action and can therefore be used as anti-inflammatory agents for treatment and/or prevention of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders and inflammatory skin disorders.

The compound of the formula (II) according to the invention and the dosage forms according to the invention are furthermore suitable for the treatment and/or prevention of acute pain, central pain syndrome, chemotherapy-induced neuropathy and neuropathic pain, diabetic neuropathy, fibromyalgia, inflammatory pain, neuropathic pain, postoperative pain, tonic pain or visceral pain.

The compound of the formula (II) according to the invention and the dosage forms according to the invention are furthermore suitable for the treatment and/or prevention of fibrotic disorders of the internal organs, for example the lung, the heart, the kidneys, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, systemic sclerosis, morphea, keloids, hypertrophic scarring, naevi, diabetic retinopathy, proliferative vitroretinopathy and disorders of the connective tissue (for example sarkoidosis). The dosage forms according to the invention can likewise be used for treating steatohepatitis, in particular non-alcoholic steatohepatitis (NASH), for promotion of wound healing, for controlling postoperative scarring, for example following glaucoma operations and cosmetically for ageing and keratinized skin.

The compound of the formula (II) according to the invention and the dosage forms according to the invention are furthermore suitable for the treatment and/or prevention of bone disorders, by way of example and preferably osteogenesis imperfecta (OI), bone fractures, impared bone healing, rickets, osteomalacia, avascular bone necrosis, Paget disease, osteodystrophy, osteopenia, osteolytic lesions caused by bone metastases, radiation therapy or chemotherapy, parodontitis, hypercalcaemia, osteonecrosis, osteosarcoma, osteolytic metastases, familiar expansive osteolysis, expansive skeletal and idiopathic hyperplasia, juvenile Paget disease, Camurati-Engelmann disease, loosening of prostheses, periprostetic osteolysis, cleidocranial dysplasia (CCD), multiple myeloma, alveolar bone loss, bone loss owing to immobilization or sexual hormone deficiency, bone loss associated with a disease selected from the group consisting of cachexia, anorexia, alopecia and inflammatory disorders selected from the group consisting of rheumatoid arthritis, psoriatic arthritis, psoriasis, spondyloarthritis, SLE, systemic sclerosis, metastasizing cancer and inflammatory bowel disease, osteoarthritis, impaired bone healing after osteotomy, idiopathic bone loss in infancy, deformed spine, osteoporosis, primary osteoporosis, secondary osteoporosis and in particular osteoporosis, primary osteoporosis or secondary osteoporosis not caused by sexual hormone deficiency.

The compound of the formula (II) according to the invention and the dosage forms according to the invention are furthermore suitable for the treatment and/or prevention of dysfunctions of gastrointestinal sphincters, such as achalasia, sphincter spasms and hypertensive sphincter, in particular lower oesophagus sphincter (LES) achalasia, oesophagus achalasia, spastic LES, hypertensive LES (HTNLES), pylorus sphincter (pylorus) achalasia, pylorus spasm (pylorospasm), hypertensive pylorus, ileocaecal sphincter or valve (ICV) achalasia, hypertensive ICV, spastic ICV or ICV spasm, sphincter of Oddi dysfunction (SOD), sphincter of Oddi achalasia, spastic sphincter of Oddi, hypertensive sphincter of Oddi, internal anal sphincter (IAS) achalasia, hypertensive IAS, spastic IAS or IAS cramp. In a further embodiment, the gastrointestinal sphincter dysfunctions mentioned are caused by a neurological, metabolic, endocrine or neurodegenerative disorder.

By virtue of their activity profile, the compound of the formula (II) according to the invention and the dosage forms according to the invention are suitable in particular for the treatment and/or prevention of cardiovascular and cardiopulmonary disorders such as primary and secondary forms of pulmonary hypertension, heart failure, angina pectoris and hypertension and also of thromboembolic disorders, ischaemias, vascular disorders, impaired microcirculation, renal insufficiency, fibrotic disorders and arteriosclerosis.

Preferably, the compound of the formula (II) according to the invention and the dosage forms according to the invention are suitable for the treatment and/or prevention of cardiovascular disorders, in particular heart failure including heart failure with reduced ejection fraction (HFrEF) and heart failure with preserved ejection fraction (HFpEF).

Preferably, the compound of the formula (II) according to the invention and the dosage forms according to the invention are suitable for the treatment and/or prevention of cardiopulmonary disorders, in particular pulmonary hypertension.

Preferably, the compound of the formula (II) according to the invention and the dosage forms according to the invention are suitable for the treatment and/or prevention of disorders of the central nervous system, in particular dementia including vascular dementia and mixed forms of dementia.

Preferably, the compound of the formula (II) according to the invention and the dosage forms according to the invention are suitable for the treatment and/or prevention of "muscular or neuromuscular disorders", in particular Duchenne muscular dystrophy (DMD) and Becker muscular dystrophy (BMD).

The present invention furthermore provides the use of the compound of the formula (II) according to the invention and the dosage forms according to the invention for the treatment and/or prevention of sickle cell anaemia, where traumatized patients receive a synthetic blood substitute, and for preservation of blood substitutes.

The present invention furthermore provides the use of the compound of the formula (II) according to the invention and the dosage forms according to the invention for the treatment and/or prevention of polycystic ovary syndrome (PCOS).

The present invention furthermore provides the use of the compound of the formula (II) according to the invention and the dosage forms according to the invention for the treatment and/or prevention of preeclampsia.

The present invention furthermore provides the use of the compound of the formula (II) according to the invention and the dosage forms according to the invention for the treatment and/or prevention of disorders, especially of the aforementioned disorders.

The present invention furthermore provides the use of the compound of the formula (II) according to the invention and the dosage forms according to the invention in a method for treatment and/or prevention of disorders, especially of the aforementioned disorders.

The present invention further provides a process for treatment and/or prevention of disorders, especially of the aforementioned disorders, using an effective amount of the compound of the formula (II) according to the invention or at least one of the dosage forms according to the invention.

The compound of the formula (II) according to the invention or the dosage forms according to the invention can be used alone or, if required, in combination with other active compounds. The present invention further provides medicaments comprising at least one of the dosage forms according to the invention and one or more further active compounds, especially for the treatment and/or prophylaxis of the aforementioned disorders. Preferred examples of active compounds suitable for combinations include:

organic nitrates and NO donors, for example sodium nitroprusside, nitroglycerin, isosorbide mononitrate, isosorbide dinitrate, molsidomine or SIN-1, and inhaled NO;

further substances which increase the cGMP concentration, for example protoporphyrine IX, arachidonic acid or phenylhydrazine derivatives;

NO synthase substrates, for example N-hydroxyguanidine derivatives, L-arginine derivatives, N-alkyl-N'-hydroxyguanidine derivatives, N-aryl-N'-hydroxyguanidine derivatives or guanidine derivatives;

compounds which inhibit the degradation of cyclic guanosine monophosphate (cGMP) and/or cyclic adenosine monophosphate (cAMP), for example inhibitors of phosphodiesterases (PDE) 1, 2, 3, 4, 5, 9 and/or 10, especially PDE 4 inhibitors such as roflumilast or revamilast and PDE 5 inhibitors such as sildenafil, vardenafil, tadalafil, udenafil, dasantafil, avanafil, mirodenafil or lodenafil;

NO-independent but haem-dependent stimulators of guanylate cyclase, especially riociguat, nelociguat, vericiguat, praliciguat (IW-1973), olinciguat (IW-1701) and the in WO 00/06568, WO 00/06569, WO 02/42301, WO 03/095451, WO 2011/147809, WO 2012/004258, WO 2012/028647 and WO 2012/059549;

prostacyclin analogues and IP receptor agonists, by way of example and with preference iloprost, beraprost, treprostinil, epoprostenol, NS-304, selexipag or ralinepag;

endothelin receptor antagonists, by way of example and with preference bosentan, darusentan, ambrisentan, macicentan or sitaxsentan;

inhibitors of human neutrophil elastase (HNE), by way of example and with preference sivelestat or DX-890 (Reltran);

compounds which inhibit the signal transduction cascade, in particular from the group of the tyrosine kinase inhibitors, by way of example and with preference dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib, masitinib or tandutinib;

Rho kinase inhibitors, by way of example and with preference fasudil, Y-27632, SLx-2119, BF-66851, BF-66852, BF-66853, KI-23095 or BA-1049;

anti-obstructive agents as used, for example, for the therapy of chronic obstructive pulmonary disease (COPD) or bronchial asthma, by way of example and with preference, inhalatively or systemically administered beta-receptor mimetics (e.g. bedoradrine) or inhalatively administered anti-muscarinergic substances;

anti-inflammatory and/or immunosuppressive agents as used, for example, for the therapy of chronic obstructive pulmonary disease (COPD), bronchial asthma or pulmonary fibrosis, such as, by way of example and with preference, systemically or inhalatively administered corticosteroids, flutiform, pirfenidone, acetylcysteine, azathioprine or BIBF-1120;

chemotherapeutics like those employed, for example, for the therapy of neoplasms in the lung or other organs;

active compounds used for the systemic and/or inhalative treatment of pulmonary disorders, for example for cystic fibrosis (alpha-1-antitrypsin, aztreonam, ivacaftor, lumacaftor, ataluren, amikacin, levofloxacin), chronic obstructive pulmonary disease (COPD) (LAS40464, PT003, SUN-101), acute respiratory distress syndrome (ARDS) and acute lung injury (ALI) (interferon-beta-la, traumakines), obstructive sleep apnoea (VI-0521), bronchiectasis (mannitol, ciprofloxacin), bronchiolitis obliterans (cyclosporin, aztreonam) and sepsis (pagibaximab, Voluven, ART-123);

active compounds used for the treatment of muscular dystrophy, for example idebenone;

antithrombotic agents, by way of example and with preference from the group of the platelet aggregation inhibitors, the anticoagulants or the profibrinolytic substances;

active compounds altering lipid metabolism, for example and with preference from the group of the thyroid receptor agonists, cholesterol synthesis inhibitors, by way of example and preferably HMG-CoA reductase inhibitors or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists;

active compounds which inhibit neoangiogenesis, by way of example and with preference inhibitors of the VEGF and/or PDGF signalling pathways, inhibitors of the integrin signalling pathways, inhibitors of the angiopoietin-Tie signalling pathways, inhibitors of the PI3K-Akt-mTor signalling pathways, inhibitors of the Ras-Raf-Mek-Erk signalling pathway, inhibitors of the MAPK signalling pathways, inhibitors of the FGF signalling pathways, inhibitors of the sphingosine-1-phosphate signalling pathways, inhibitors of endothelial cell proliferation or apoptosis-inducing active ingredients;

active compounds which reduce vascular wall permeability (oedema formation), by way of example and with preference corticosteroids, inhibitors of the ALK1-Smad1/5 signalling pathway, inhibitors of the VEGF and/or PDGF signalling pathways, cyclooxygenase inhibitors, inhibitors of the kallikrein-kinin system or inhibitors of the sphingosine-1-phosphate signalling pathways;

active compounds which reduce damage to the retina under oxidative stress, by way of example and with preference inhibitors of the complement system, especially antagonists of the complement C5a receptor, or agonists of the $5-HT_{1A}$ receptor;

antioxidants and free-radical scavengers;

active hypotensive compounds, by way of example and with preference from the group of the calcium antagonists, angiotensin AII antagonists, ACE inhibitors, beta-receptor blockers, alpha-receptor blockers, diuretics, phosphodiesterase inhibitors, sGC stimulators, cGMP elevators, ECE inhibitors, vasopeptidase inhibitors and/or mineralocorticoid receptor antagonists;

antiarrhythmic agents, for example sodium channel blockers, beta-receptor blockers, potassium channel blockers or calcium channel blockers;

alpha-1-adrenoceptor antagonists;

centrally acting alpha-2-adrenoceptor agonists;

imidazoline I-1 receptor agonists;

dopamine D1 receptor agonists;

5-HT2 antagonists;

vasopressin antagonists;

calcium channel sensitizers;

bronchodilators, for example beta-2-adrenoceptor agonists, anticholinergics, theopylline or PDE inhibitors;
corticosteroids, for example prednisolone;
PGD2 receptor antagonists;
non-steroidal antiasthmatics, for example beta-2-adrenoceptor agonists or combinations of beta-2-adrenoceptor agonists and corticosteroids;
non-steroidal anti-inflammatory drugs (NSAIDs) and selective cyclooxigenase-2 (COX-2) inhibitors;
medicaments for excess weight and obesity, for example methamphetamine, amfepramon, phentermine, benzphetamine, phendimetrazine, mazindol, orlistat, sibutramine or rimonabant and combinations such as, for example, phentermine/topiramate, bupropion/naltrexone, sibutramine/metformin, bupropion SR/zonisamide SR, salmeterol, xinafoate/fluticasone; lorcaserin, phentermine/topiramate, cetilistat, exenatide, liraglutide, metformin, sibutramine/metformin, bupropion SR/zonisamide SR, CORT-108297, canagliflozin, chromium picolinate, GSK-1521498, LY-377604, metreleptin, obinepitide, P-S7AS3, PSN-821, salmeterol xinafoate/fluticasone, somatropin (recombinant), tesamorelin, tesofensine, velneperit, zonisamide, beloranib, resveratrol, sobetirome, tetrahydrocannabivarin and beta-lapachone;
adenylate cyclase inhibitors, for example colforsin dapropate;
positive inotropic substances, for example digoxin;
medicaments for the treatment of erectile dysfunction, for example alprostadil;
drugs for dementia such as acetylcholinesterase inhibitors, for example donepezil, galantamine and rivastigmine; or NMDA receptor antagonists, for example memantine;
medicaments for the treatment of mental disorders, for example dopamine D4 receptor antagonists such as clozapine, dopamine D2 receptor antagonists, such as nemonaprid, mixed dopamine D1/D2 receptor antagonists such as zuclopenthixol, GABA A receptor modulators such as carbamazepine, sodium channel inhibitors such as lamotrigine, monoamine oxidase inhibitors such as moclobemide, tricyclic antidepressants such as amitriptyline, desipramine, imipramine, amoxapine, nortriptyline or clomipramine, selective serotonin reuptake inhibitors (SSRIs) such as paroxetine, fluoxetine or citralopram, doxepine, trazodone or agomelatine, selective noradrenaline reuptake inhibitors (SNRIs) such as venlafaxine or dopaminergic antidepressants such as bupropion;
inhibitors of neural endopeptidase (NEP inhibitors) such as sacubitril, omapatrilate or methylene blue, AVE-7688, or in dual combination ('ARNIs') with angiotensin receptor blockers (e.g. valsartan), e.g. LCZ696;
natriuretic peptides, for example atrial natriuretic peptide (ANP, anaritide), B-type natriuretic peptide or brain natriuretic peptide (BNP, nesiritide), C-type natriuretic peptide (CNP) and urodilatin;
antidiabetics, by way of example and with preference from the group of the insulins and insulin derivatives, sulphonylureas, biguanides, meglitinide derivatives, glucosidase inhibitors, PPAR-gamma agonists, GLP 1 receptor agonists, glucagon antagonists, insulin sensitizers, CCK1 receptor agonists, inhibitors of dipeptidylpeptidase 4 (gliptins), SGLT 2 inhibitors, leptin receptor agonists, potassium channel antagonists and the inhibitors of hepatic enzymes that are involved in the stimulation of gluconeogenesis and/or glycogenolysis;
anti-infectives, by way of example and with preference from the group of the antibacterial, antifungal and/or antiviral active substances; and/or
substances for treatment of glaucoma, by way of example and with preference from the group of the adrenergics, beta-receptor blockers, carbonic anhydrase inhibitors, parasympathomimetics and prostaglandins; and/or
substances for the treatment of bone disorders, by way of example and with preference bisphosphonates, vitamin D or its metabolites, strontium ranelate, selective oestrogen receptor modulators (SERM), parathyroid hormone or analogues thereof and/or RANKL (receptor activator of nuclear factor kappa-B ligand) modulators.

Antithrombotic agents are preferably understood to mean compounds from the group of the platelet aggregation inhibitors, the anticoagulants or the profibrinolytic substances.

In a preferred embodiment of the invention, the compound of the formula (II) according to the invention or the dosage forms according to the invention are administered in combination with a platelet aggregation inhibitor, by way of example and with preference aspirin, clopidogrel, ticlopidine or dipyridamole.

In a preferred embodiment of the invention, the compound of the formula (II) according to the invention or the dosage forms according to the invention are administered in combination with a thrombin inhibitor, by way of example and with preference ximelagatran, melagatran, dabigatran, bivalirudin or clexane.

In a preferred embodiment of the invention, the compound of the formula (II) according to the invention or the dosage forms according to the invention are administered in combination with a GPIIb/IIIa antagonist, by way of example and with preference tirofiban or abciximab.

In a preferred embodiment of the invention, the compound of the formula (II) according to the invention or the dosage forms according to the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compound of the formula (II) according to the invention or the dosage forms according to the invention are administered in combination with heparin or a low molecular weight (LMW) heparin derivative.

In a preferred embodiment of the invention, the compound of the formula (II) according to the invention or the dosage forms according to the invention are administered in combination with a vitamin K antagonist, by way of example and with preference coumarin, phenprocumon or warfarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compound of the formula (II) according to the invention or the dosage forms according to the invention are administered in combination with a calcium antagonist, by way of example and with preference nifedipine, amlodipine, verapamil or diltiazem.

In a preferred embodiment of the invention, the compound of the formula (II) according to the invention or the dosage forms according to the invention are administered in combination with an alpha 1 adrenoceptor antagonist, by way of example and with preference prazosin.

In a preferred embodiment of the invention, the compound of the formula (II) according to the invention or the dosage forms according to the invention are administered in combination with a beta receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compound of the formula (II) according to the invention or the dosage forms according to the invention are administered in combination with an angiotensin AII antagonist, by way of example and with preference losartan, candesartan, valsartan, telmisartan or embursatan.

In a preferred embodiment of the invention, the dosage forms according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compound of the formula (II) according to the invention or the dosage forms according to the invention are administered in combination with an endothelin antagonist, by way of example and with preference bosentan, darusentan, ambrisentan or sitaxsentan.

In a preferred embodiment of the invention, the compound of the formula (II) according to the invention or the dosage forms according to the invention are administered in combination with a renin inhibitor, by way of example and with preference aliskiren, SPP-600 or SPP-800.

the compound of the formula (II) according to the invention or the dosage forms according to the invention are administered in combination with a mineralocorticoid receptor antagonist, for example spironolactone or eplerenone, particularly preferably with a non-steroidal mineralocorticoid receptor antagonist such as finerenone.

In a preferred embodiment of the invention, the compound of the formula (II) according to the invention or the dosage forms according to the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the compound of the formula (II) according to the invention or the dosage forms according to the invention are administered in combination with a CETP inhibitor, by way of example and with preference torcetrapib (CP-5294/4), JJT-705 or CETP vaccine (Avant).

In a preferred embodiment of the invention, the compound of the formula (II) according to the invention or the dosage forms according to the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compound of the formula (II) according to the invention or the dosage forms according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compound of the formula (II) according to the invention or the dosage forms according to the invention are administered in combination with a squalene synthesis inhibitor, by way of example and with preference BMS-188494 or TAK-475.

In a preferred embodiment of the invention, the compound of the formula (II) according to the invention or the dosage forms according to the invention are administered in combination with an ACAT inhibitor, by way of example and with preference avasimib, melinamide, pactimib, eflucimib or SMP-797.

In a preferred embodiment of the invention, the compound of the formula (II) according to the invention or the dosage forms according to the invention are administered in combination with an MTP inhibitor, by way of example and with preference implitapide, BMS-201038, R-103757 or JTT-130.

In a preferred embodiment of the invention, the compound of the formula (II) according to the invention or the dosage forms according to the invention are administered in combination with a PPAR-gamma agonist, by way of example and with preference pioglitazone or rosiglitazone.

In a preferred embodiment of the invention, the compound of the formula (II) according to the invention or the dosage forms according to the invention are administered in combination with a PPAR-delta agonist, by way of example and with preference GW 501516 or BAY 68-5042.

In a preferred embodiment of the invention, the compound of the formula (II) according to the invention or the dosage forms according to the invention are administered in combination with a cholesterol absorption inhibitor, by way of example and with preference ezetimib, tiqueside or pamaqueside.

In a preferred embodiment of the invention, the compound of the formula (II) according to the invention or the dosage forms according to the invention are administered in combination with a lipase inhibitor, by way of example and with preference orlistat.

In a preferred embodiment of the invention, the compound of the formula (II) according to the invention or the dosage forms according to the invention are administered in combination with a polymeric bile acid adsorber, by way of example and with preference cholestyramine, colestipol, colesolvam, Cholestagel or colestimide.

In a preferred embodiment of the invention, the compound of the formula (II) according to the invention or the dosage forms according to the invention are administered in combination with a bile acid reabsorption inhibitor, by way of example and with preference ASBT (=IBAT) inhibitors, e.g. AZD-7806, S-8921, AK-105, BARI-1741, SC-435 or SC-635.

In a preferred embodiment of the invention, the compound of the formula (II) according to the invention or the dosage forms according to the invention are administered in combination with a lipoprotein(a) antagonist, by way of example and with preference gemcabene calcium (CI-1027) or nicotinic acid.

In a preferred embodiment of the invention, the compound of the formula (II) according to the invention or the dosage forms according to the invention are administered in combination with acetylcholinesterase inhibitors, by way of example and with preference donepezil, galantamine or rivastigmine.

In a preferred embodiment of the invention, the compound of the formula (II) according to the invention or the dosage forms according to the invention are administered in combination with NMDA receptor antagonists, by way of example and with preference memantine.

In a preferred embodiment of the invention, the compound of the formula (II) according to the invention or the dosage forms according to the invention are administered in combination with sGC stimulators, by way of example and with preference riociguat, nelociguat, vericiguat, praliciguat (IW-1973) or olinciguat (IW-1701).

In a preferred embodiment of the invention, the compound of the formula (II) according to the invention or the dosage forms according to the invention are administered in combination with antidiabetics, by way of example and with preference metformin.

In a preferred embodiment of the invention, the compound of the formula (II) according to the invention or the dosage forms according to the invention are administered in combination with SGLT-2 inhibitors, by way of example and with preference dapagliflozin, empagliflozin, canagliflozin, ipragliflozin and/or tofogliflozin.

In a preferred embodiment of the invention, the compound of the formula (II) according to the invention or the dosage forms according to the invention are in combination with substances for the treatment of bone disorders such as, by way of example and with preference vitamin D or metabolites thereof, strontium ranelate, selective oestrogen receptor modulators (SERM) and/or RANKL modulators.

In a preferred embodiment of the invention, the compound of the formula (II) according to the invention or the dosage forms according to the invention are in combination with bisphosphonates, by way of example and with preference etidronate, clodronate, tiludronate, teriparatide, pamidronate, neridronate, olpadronate, alendronate, ibandronate, risedronate, zoledronate.

The invention furthermore provides the compound of the formula (II), preferably in crystalline form of modification 1, for the treatment and/or prevention of diseases.

The invention furthermore provides the compound of the formula (II), preferably in crystalline form of modification 1, for the treatment and/or prevention of renal and cardiorenal disorders, in particular chronic kidney disease (CKD) and diabetic kidney disease (DKD), cardiac and cardiovascular disorders, in particular heart failure (HFpEF and HFrEF), myocardial infarction, angina pectoris, cardiomyopathies, hypertension and arteriosclerosis, pulmonary and cardiopulmonary disorders, in particular pulmonary hypertension (PH), disorders of the central nervous system, in particular dementia, bone disorders, in particular osteogenesis imperfecta, thromboembolic disorders, muscular dystrophies, ischaemias, vascular disorders, impaired microcirculation, fibrotic disorders, in particular systemic sclerosis, ophthalmological disorders, inflammatory disorders, and metabolic disorders, in particular metabolic syndrome, dyslipidaemia and diabetes.

The invention furthermore provides the compound of the formula (II), preferably in crystalline form of modification 1, for the treatment and/or prevention of renal and cardiorenal disorders, in particular chronic kidney disease (CKD) and diabetic kidney disease (DKD).

The invention furthermore provides the compound of the formula (II), preferably in crystalline form of modification 1, for the treatment and/or prevention of cardiac and cardiovascular disorders, in particular heart failure (HFpEF and HFrEF), myocardial infarction, angina pectoris, cardiomyopathies, hypertension and arteriosclerosis.

The invention furthermore provides the compound of the formula (II), preferably in crystalline form of modification 1, for the treatment and/or prevention of pulmonary and cardiopulmonary disorders, in particular pulmonary hypertension (PH).

The invention furthermore provides the compound of the formula (II), preferably in crystalline form of modification 1, for the treatment and/or prevention of disorders of the central nervous system, in particular dementia.

The invention furthermore provides the compound of the formula (II), preferably in crystalline form of modification 1, for the treatment and/or prevention of disorders of the central nervous system, in particular vascular and Alzheimer dementia.

The invention furthermore provides the compound of the formula (II), preferably in crystalline form of modification 1, for the treatment and/or prevention of metabolic disorders, in particular metabolic syndrome, dyslipidaemia and diabetes.

The invention furthermore provides the use of an osmotic release system according to the invention comprising the compound of the formula (II), preferably in crystalline form of modification 1, for the treatment and/or prevention of diseases.

The invention furthermore provides the use of an osmotic release system according to the invention comprising the compound of the formula (II), preferably in crystalline form of modification 1, for the treatment and/or prevention of renal and cardiorenal disorders, in particular chronic kidney disease (CKD) and diabetic kidney disease (DKD), cardiac and cardiovascular disorders, in particular heart failure (HFpEF and HFrEF), myocardial infarction, angina pectoris, cardiomyopathies, hypertension and arteriosclerosis, pulmonary and cardiopulmonary disorders, in particular pulmonary hypertension (PH), disorders of the central nervous system, in particular dementia, bone disorders, in particular osteogenesis imperfecta, thromboembolic disorders, muscular dystrophies, ischaemias, vascular disorders, impaired microcirculation, fibrotic disorders, in particular systemic sclerosis, ophthalmological disorders, inflammatory disorders, and metabolic disorders, in particular metabolic syndrome, dyslipidaemia and diabetes.

The invention furthermore provides the use of an osmotic release system according to the invention comprising the compound of the formula (II), preferably in crystalline form of modification 1, for the treatment and/or prevention of renal and cardiorenal disorders, in particular chronic kidney disease (CKD) and diabetic kidney disease (DKD).

The invention furthermore provides the use of an osmotic release system according to the invention comprising the compound of the formula (II), preferably in crystalline form of modification 1, for the treatment and/or prevention of cardiac and cardiovascular disorders, in particular heart failure (HFpEF and HFrEF), myocardial infarction, angina pectoris, cardiomyopathies, hypertension and arteriosclerosis.

The invention furthermore provides the use of an osmotic release system according to the invention comprising the compound of the formula (II), preferably in crystalline form of modification 1, for the treatment and/or prevention of pulmonary and cardiopulmonary disorders, in particular pulmonary hypertension (PH).

The invention furthermore provides the use of an osmotic release system according to the invention comprising the compound of the formula (II), preferably in crystalline form of modification 1, for the treatment and/or prevention of disorders of the central nervous system, in particular dementia.

The invention furthermore provides the use of an osmotic release system according to the invention comprising the compound of the formula (II), preferably in crystalline form of modification 1, for the treatment and/or prevention of disorders of the central nervous system, in particular vascular and Alzheimer dementia.

The invention furthermore provides the use of an osmotic release system according to the invention comprising the compound of the formula (II), preferably in crystalline form of modification 1, for the treatment and/or prevention of metabolic disorders, in particular metabolic syndrome, dyslipidaemia and diabetes.

The invention furthermore provides medicaments comprising the compound of the formula (II) in combination with one or more other active ingredients selected from the group consisting of organic nitrates, NO donors, cGMP-PDE inhibitors, stimulators of guanylate cyclase, antithrombotics, antihypertensive agents, MR antagonists, IP receptor agonists, compounds having anti-inflammatory action, antidementives, antidiabetics, active compounds which modify fat metabolism and active compounds for the treatment of bone and muscle disorders.

In the dosage forms according to the invention, the compound of the formula (II) is preferably present in an amount of about 1 to 120 mg, particularly preferably in an amount of 2.5 mg to 50 mg. The present invention provides the above-mentioned pharmaceutical dosage forms according to the invention comprising the compound of the formula (II) preferably in an amount of 1 mg, 2 mg, 2.5 mg, 3 mg, 4 mg, 5 mg, 6 mg, 7 mg, 8 mg, 9 mg, 10 mg, 12 mg, 15 mg, 20 mg, 25 mg, 30 mg, 35 mg, 40 mg, 50 mg, 60 mg, 70 mg, 75 mg, 80 mg, 90 mg, 100 mg, 110 mg and 120 mg. The amounts of the compound of the formula (II) refer to the nominal amounts in the pharmaceutical dosage form, in certain circumstances an excess of up to 20% of the amount of active ingredient may additionally be present.

In general, it has been found to be advantageous to administer about 0.01 to 10 mg/kg of body weight per day to obtain effective results.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the aforementioned minimum amount, while in other cases the upper limit mentioned must be exceeded. In the case of administration of greater amounts, it may be advisable to divide them into several individual doses over the day.

EXPERIMENTAL SECTION

Abbreviations and Acronyms cp centipoise
HPLC high-pressure/high-performance liquid chromatography
K Kelvin
min minute
ml milliliter
µl microliter
mm millimeter
m micrometer
mPa millipascal
s second
r revolution
USP United States Pharmacopeia
UV ultraviolet

WORKING EXAMPLES

Exemplary Compound 1

Sodium (3S)-3-(4-chloro-3-{[(2S,3R)-2-(4-chlorophenyl)-4,4,4-trifluoro-3-methylbutanoyl]amino}phenyl)-3-cyclopropylpropanoate in crystalline modification 1

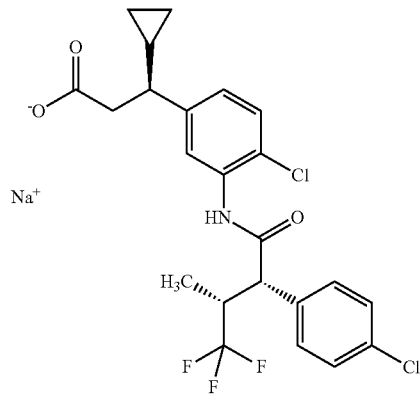

Preparation Method 1

Under a nitrogen atmosphere, a reaction vessel was filled with 1425 g of the compound of the formula (I) (preparation disclosed in WO 2012/139888, Example 22 and EP17204842.3) and 13.3 kg of acetonitrile. The mixture is stirred until a solution has formed. 117 g of solid sodium hydroxide are added and the resulting suspension is stirred vigorously for 25 hours. The suspension is filtered. The solids obtained are washed with 1.2 kg of acetonitrile and dried under reduced pressure at 30° C. for 19 hours.

Yield: 1375 g (92%)
Content of the compound of the formula (II): 96.4% (HPLC Method 1)
Content of the compound of the formula (III): <0.20% (HPLC Method 2)
Sodium content: 4.8%
XRPD: modification 1

Preparation Method 2

Under a nitrogen atmosphere, a reaction vessel is filled with 34.4 kg of acetonitrile and 4.0 kg of the compound of the formula (I) (content determination 99.1%) (preparation disclosed in WO 2012/139888, Example 22 and EP17204842.3). The mixture is stirred at 20° C. The resulting solution is filtered and the filter is washed with 3 kg of acetonitrile. The filtrate is cooled to 0° C. 3.9 kg of a tetrahydrofuran solution of sodium tert-butoxide (content determination 19.6%) are added slowly at a temperature of from −5° C. to +5° C. After addition of about ⅔ of the sodium tert-butoxide solution, seed crystals of the compound of the formula (II) in crystalline modification 1 are added. After completion of the metered addition, the line used for the metered addition is rinsed with an additional 3.0 kg of tetrahydrofuran. The resulting mixture is stirred at 0° C. for 17 hours. The suspension is filtered and the solids obtained are washed twice with 5.6 kg of cold acetonitrile. The product is dried under reduced pressure at 40° C. for 16 hours.

Yield: 4.0 kg (97%)

Content of the compound of the formula (II): 98.7% (HPLC Method 1)

Content of the compound of the formula (III): 0.19% (HPLC Method 2)

Sodium content: 4.4%

XRPD: modification 1

Analytical Methods

HPLC Method 1:

The tests for content determination and for impurities are carried out on a reversed-phase HPLC column with UV detection at 210 nm. The stationary phase is a Zorbax Eclipse Plus RRHD C18 HPLC column (50 mm×2.1 mm, particle size 1.8 rpm) or a suitable alternative.

Gradient elution was chosen for optimal separation of the maxima. The gradient of the mobile phase is shown in Table 1 below.

Mobile phase A is water with 0.1% trifluoroacetic acid, mobile phase B is acetonitrile with 0.1% trifluoroacetic acid.

TABLE 1

| Time [min] | % A | % B |
|---|---|---|
| 0.0 | 95 | 5 |
| 25.0 | 20 | 80 |

The flow rate is 1.0 ml/min, the column temperature is 20° C., the injection volume is 2 μl. Test solutions are prepared by dissolution in a mixture of equal parts of acetonitrile and water to a concentration of 0.46 mg/ml.

Quantification is carried out either by external calibration using a reference standard or via mass balance. The retention time of the compound of the formula (II) is about 16.2 min, the retention time of the compound of the formula (III) is about 12.0 min.

HPLC Method 2:

The tests for impurities are carried out on a normal-phase HPLC column with UV detection at 220 nm. The stationary phase is a Chiralpak AD-H HPLC column (250 mm×4.6 mm, particle size 5 m) or a suitable alternative.

Isocratic elution was chosen for optimal separation of the maxima.

The mobile phase consists of 93% by volume of isohexane and 7% by volume of a mixture of 2-propanol with 0.2% trifluoroacetic acid and 1% water.

The flow rate is 1.25 ml/min, the column temperature is 30° C., the injection volume is 5 μl. Test solutions are prepared by dissolution in a mixture of isohexane and 2-propanol (3/1, by volume) to a concentration of 0.5 mg/ml.

Quantification is carried out by external calibration using a reference standard. The retention time of the compound of the formula (II) is about 11.4 min, the retention time of the compound of the formula (III) is about 9.7 min.

Method 3 (Sodium Analysis):

Sodium is analysed by an ICP-MS method as semiquantitative summary analysis. Sample preparation takes place by microwave digestion with nitric acid.

Method 4—X-Ray Diffractometry for the Measurement of the Compound of the Formula (I) in Crystalline Form of Modification 1:

| | |
|---|---|
| Sample preparation: | sample as even powder layer between two films. |
| Instrument: | X-ray powder diffractometer (STOE STADI P) |
| Generator: | 40 kV/40 mA |
| Detector: | location-sensitive detector |
| Radiation: | germanium-monochromatized CuKa1 radiation |
| Measurement mode: | transmittance |
| Measurement range: | 2° ≤ 2θ ≤ 40° |
| Step width: | 0.5° |
| Measurement time: | 15 s/step |

TABLE 2

X-ray diffractometry of the compound of the formula (I) in crystalline modification 1

| Reflections Modification 1 | | | | | |
|---|---|---|---|---|---|
| 6.5 | 17.2 | 24.1 | 28.6 | 32.7 | 38.1 |
| 7.6 | 17.5 | 24.4 | 28.8 | 33.1 | 38.5 |
| 8.1 | 18.0 | 24.7 | 29.0 | 33.7 | 38.7 |
| 9.6 | 18.8 | 25.1 | 29.3 | 34.0 | 38.9 |
| 10.3 | 19.4 | 25.2 | 29.5 | 34.7 | 39.4 |
| 11.0 | 19.8 | 25.5 | 29.8 | 35.5 | 39.6 |
| 14.7 | 21.0 | 25.8 | 30.4 | 35.8 | 39.8 |
| 15.1 | 21.4 | 26.5 | 30.8 | 36.1 | |
| 15.6 | 21.7 | 26.8 | 31.2 | 36.3 | |
| 16.0 | 22.3 | 27.2 | 31.6 | 36.7 | |
| 16.4 | 22.6 | 28.1 | 32.3 | 37.7 | |

Figure 5:
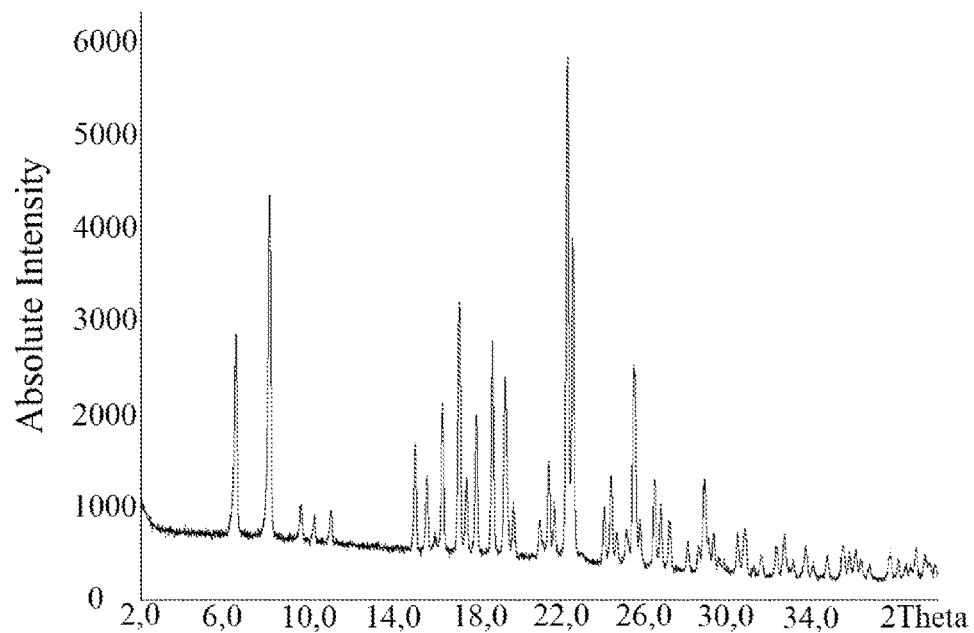
FIG. 5 shows the X-ray diffractogram of the compound of the formula (I) in crystalline modification 1.

The X-ray diffractogram of the compound of the formula (I) in crystalline modification 1 is shown in FIG. 5.

Method 5—IR Spectroscopy for the Measurement of the Compound of the Formula (I) in Crystalline Form of Modification 1:

| | |
|---|---|
| Sample preparation: | Sample was prepared as KBr disc |
| Instrument | Bruker Vertex 80v |
| Number of scans | 32 |
| Resolution | 2 cm$^{-1}$ |
| Technique | transmission |

TABLE 3

IR spectra of the compound of the formula (I) in crystalline modification 1

| Band maximum [cm$^{-1}$] Modification 1 | | | | | |
|---|---|---|---|---|---|
| 3381 | 1524 | 1245 | 975 | 735 | 532 |
| 3066 | 1492 | 1185 | 937 | 721 | 516 |
| 2997 | 1458 | 1169 | 906 | 712 | 492 |
| 2975 | 1419 | 1135 | 895 | 669 | 447 |
| 2954 | 1389 | 1108 | 844 | 654 | 422 |
| 2914 | 1376 | 1101 | 827 | 628 | |
| 1691 | 1312 | 1069 | 817 | 593 | |
| 1595 | 1286 | 1044 | 788 | 566 | |
| 1565 | 1263 | 1022 | 753 | 546 | |

Figure 6:
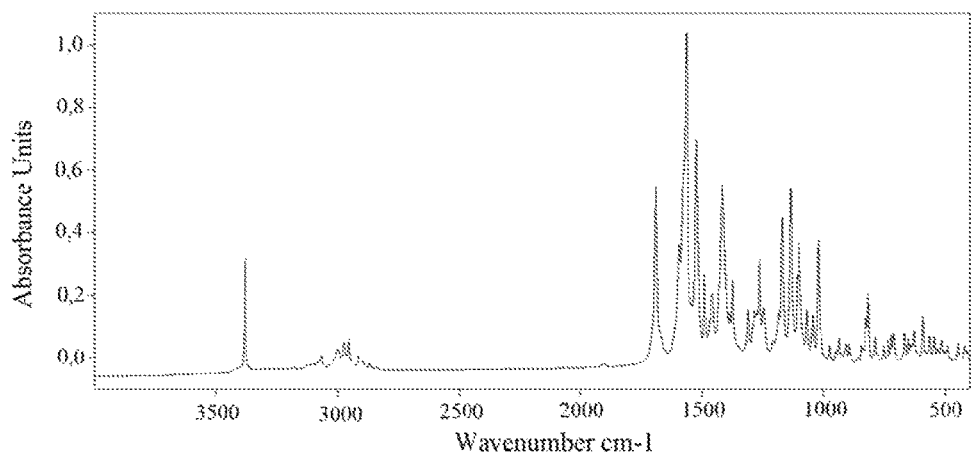
FIG. 6 shows the IR spectrum of the compound of the formula (I) in crystalline modification 1.

The IR spectrum of the compound of the formula (I) in crystalline modification 1 is shown in FIG. 6.

Osmotic release systems and the preparation thereof are shown below.

| Osmotic release system 1 Tablet composition in mg/tablet | |
|---|---|
| Core | |
| Active ingredient layer | |
| compound of the formula (II), micronized | 2.75 mg |
| hydroxypropylmethylcellulose (5 cp) | 5.70 mg |
| polyethylene oxide* | 100.45 mg |
| finely divided silica (Aerosil 200, Degussa) | 0.90 mg |
| magnesium stearate | 0.30 mg |
| | 110.1 mg |
| Osmosis layer | |
| hydroxypropylmethylcellulose (5 cp) | 3.69 mg |
| sodium chloride | 21.51 mg |
| polyethylene oxide** | 47.60 mg |
| iron oxide red | 0.72 mg |
| magnesium stearate | 0.18 mg |
| | 73.70 mg |
| total (core) | 183.8 mg |
| Shell | |
| cellulose acetate | 12.40 mg |
| polyethylene glycol 3350 | 1.60 mg |
| | 14.0 mg |
| total | 197.8 mg |

After about 5 to 6 hours, 80% of the compound of the formula (II) had been released.

| Osmotic release system 2 Tablet composition in mg/tablet | |
|---|---|
| Core | |
| Active ingredient layer | |
| compound of the formula (II), micronized | 6.00 mg |
| hydroxypropylmethylcellulose (5 cp) | 5.70 mg |
| polyethylene oxide* | 97.40 mg |
| finely divided silica (Aerosil 200, Degussa) | 0.90 mg |
| magnesium stearate | 0.30 mg |
| | 110.3 mg |
| Osmosis layer | |
| hydroxypropylmethylcellulose (5 cp) | 3.69 mg |
| sodium chloride | 21.51 mg |
| polyethylene oxide** | 47.60 mg |
| iron oxide red | 0.72 mg |
| magnesium stearate | 0.18 mg |
| | 73.7 mg |
| total (core) | 184.0 mg |
| Shell | |
| cellulose acetate | 12.60 mg |
| polyethylene glycol 3350 | 1.40 mg |
| | 14.0 mg |
| total (osmotic release system) | 198.0 mg |

After about 5 hours, 80% of the compound of the formula (II) had been released.

| Osmotic release system 3 Tablet composition in mg/tablet: | |
|---|---|
| The composition of the active ingredient layer and the osmosis layer (core) corresponds to Working Example 2. | |
| Shell | |
| cellulose acetate | 25.20 mg |
| polyethylene glycol 3350 | 2.80 mg |
| | 28.0 mg |
| total (osmotic release system) | 212.0 mg |

| Osmotic release system 4 Tablet composition in mg/tablet: | |
|---|---|
| The composition of the active ingredient layer and the osmosis layer (core) corresponds to Working Example 2. | |
| Shell | |
| cellulose acetate | 34.20 mg |
| polyethylene glycol 3350 | 3.80 mg |
| | 38.0 mg |
| total (osmotic release system) | 222.0 mg |

After about 15 hours, 80% of the compound of the formula (II) had been released.

| Osmotic release system 5 Tablet composition in mg/tablet | |
|---|---|
| Core | |
| Active ingredient layer | |
| compound of the formula (II), micronized | 5.75 mg |
| hydroxypropylmethylcellulose (5 cp) | 5.70 mg |
| polyethylene oxide* | 97.65 mg |
| finely divided silica (Aerosil 200, Degussa) | 0.90 mg |
| magnesium stearate | 0.30 mg |
| | 110.3 mg |
| Osmosis layer | |
| hydroxypropylmethylcellulose (5 cp) | 3.69 mg |
| sodium chloride | 21.51 mg |
| polyethylene oxide** | 47.60 mg |
| iron oxide red | 0.72 mg |
| magnesium stearate | 0.18 mg |
| | 73.7 mg |
| total (core) | 184.0 mg |
| Shell | |
| cellulose acetate | 27.00 mg |
| polyethylene glycol 3350 | 3.00 mg |
| | 30.0 mg |
| total (osmotic release system) | 214.0 mg |

After about 10 hours, 80% of the compound of the formula (II) had been released.

Osmotic release system 6
Tablet composition in mg/tablet

| Core | |
|---|---|
| Active ingredient layer | |
| compound of the formula (II), micronized | 17.24 mg |
| hydroxypropylmethylcellulose (5 cp) | 5.70 mg |
| polyethylene oxide* | 86.16 mg |
| finely divided silica (Aerosil 200, Degussa) | 0.90 mg |
| magnesium stearate | 0.30 mg |
| | 110.3 mg |
| Osmosis layer | |
| hydroxypropylmethylcellulose (5 cp) | 3.69 mg |
| sodium chloride | 21.51 mg |
| polyethylene oxide** | 47.60 mg |
| iron oxide red | 0.72 mg |
| magnesium stearate | 0.18 mg |
| | 73.70 mg |
| total (core) | 184.0 mg |
| Shell | |
| cellulose acetate | 27.00 mg |
| polyethylene glycol 3350 | 3.00 mg |
| | 30.00 mg |
| total (osmotic release system) | 214.0 mg |

After about 10 hours, 80% of the compound of the formula (II) had been released.

\* viscosity 5% strength aqueous solution (25° C., Brookfield viscosimeter Model RVT, spindle No. 1, speed of rotation: 50 rpm): 40-100 mPa·s (e.g. POLYOX™ Water-Soluble Resin NF WSR N-80; Dow)

\*\* viscosity 1% strength aqueous solution (25° C., Brookfield viscosimeter Model RVF, spindle No. 2, speed of rotation: 2 rpm): 5000-8000 mPa·s (e.g. POLYOX™ Water-Soluble Resin NF WSR Coagulant; Dow)

Optionally, a coat may be applied to the osmotic release systems presented. For the osmotic release systems 5 and 6, a coat of the following composition was prepared and applied in an amount of 6 mg per osmotic release system.

| Coat | |
|---|---|
| polyvinyl alcohol | 2.4 mg |
| polyethylene glycol 3350 | 1.212 mg |
| talc | 0.888 mg |
| titanium dioxide | 1.02 mg |
| iron oxide yellow | 0.2784 mg |
| iron oxide red | 0.2016 mg |
| total (coat) | 6.0 mg |

Preparation of the Osmotic Release Systems

The osmotic release systems 1 to 6 mentioned were prepared as follows:

To produce the active ingredient layer, the compound of the formula (II) in micronized form, hydroxypropylmethylcellulose (viscosity 5 mPa·s, measured in a 2% strength aqueous solution, 25° C.) and polyethylene oxide (viscosity 40 to 100 mPa·s, measured in a 5% strength aqueous solution, 25° C.) were mixed in a blender. This premix was sieved, mixed again and then subjected to dry granulation by roller granulation and finally sieved. The granules obtained were mixed with finely divided silica (silicon dioxide, Aerosil). Addition of sieved magnesium stearate was followed by final mixing to yield the mixture ready for compression.

To produce the osmosis layer, iron oxide red, hydroxypropylmethylcellulose (viscosity 5 mPa·s, measured in a 2% strength aqueous solution, 25° C.) and polyethylene oxide (viscosity 5000 to 8000 mPa·s, measured in a 1% strength aqueous solution, 25° C.) and sodium chloride were mixed in a blender. This premix was subjected to dry granulation and then sieved. Addition of sieved magnesium stearate was followed by final mixing to yield the mixture ready for compression.

The bilayer tablets were produced by tabletting on a bilayer tabletting press. First, the tabletting press was adjusted to the tabletting weight of the active ingredient layer (lower part of the tablet). Then the granules for the osmosis layer (upper part of the tablet) were added to the pre-pressed lower part of the tablet such that the respective total tablet weight of the bilayer tablet core (diameter about 8 mm) was obtained.

To produce the shell, cellulose acetate was dissolved in acetone. An aqueous solution comprising polyethylene glycol 3350 was added to the cellulose acetate solution and they were mixed. Using a coating unit suitable for organic coatings, this solution was sprayed onto the tablet cores of the bilayer tablets.

A hole having an approximate size (diameter) of 1 mm was drilled into the shell on the side of the active ingredient layer using, for example, a semiautomatic drill. Differentiation of the active ingredient layer from the osmosis layer was possible by the colour. The active ingredient layer was white to slightly orange. Owing to the added iron oxide, the osmosis layer was orange-red.

It is optionally possible to coat with film coatings which for their part may optionally comprise auxiliaries such as pigments for colouring. To this end, polyvinyl alcohol and polyethylene glycol 3350 are dissolved in water at room temperature and mixed with stirring. Gradually, talc, titanium dioxide and iron oxide were added with stirring. The resulting coating suspension was applied to the tablet cores using a suitable coating unit, for example a smooth coater.

Release Characteristics

The release of the active ingredient from the tablets was determined by the method of US Pharmacopoeia USP 39 (Chapter <711> Dissolution) using apparatus 2 (paddle test). To determine the release rate, a tablet was introduced into each beaker of the USP apparatus 2 and the amount of active ingredient that has gone into solution, after the undissolved constituents have been filtered off, is determined by HPLC. The release medium used was phosphate buffer pH 6.8 without addition of surfactant, and the paddle stirrer of the USP apparatus 2 had a speed of rotation of 100 revolutions per minute. Unless stated otherwise, the release rate of at least six test specimens was determined. In each case, the mean amount of active ingredient released is reported.

Thermoanalytical Investigation of Binary Physical Mixtures

In order to represent compatibilities in thermoanalytical investigations, the compounds of the formulae (II) and (I) were initially charged with equal parts of hydrophilic swellable polymers in a flat round bowl and, using a pestle, ground to a homogeneous powder mixture (trituration in a ratio of 1:1, binary mixture). The hydrophilic swellable polymers investigated were polyethylene oxide, xanthan and vinylpyrrolidone/vinyl acetate copolymer (Kollidon VA64). The physical mixtures and the respective individual components were characterized thermoanalytically. The thermograms were recorded on a differential scanning calorimeter. To this end, in each case about 5 mg of the sample were heated in an aluminium pan under nitrogen (50 ml/min) using a heating rate of 10 K/min to the end of the melting point of the compound in question.

The invention claimed is:

1. A compound that is sodium (3S)-3-(4-chloro-3-{[(2S,3R)-2-(4-chlorophenyl)-4,4,4-trifluoro-3-methylbutanoyl]amino}phenyl)-3-cyclopropylpropanoate of the formula (II)

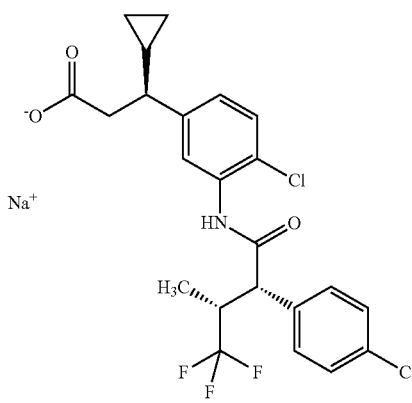

2. The compound of the formula (II) according to claim 1, in crystalline form of modification 1, characterized in that the X-ray diffractogram of the compound has peak maxima of the 2 theta angle at 8.1, 17.2, 18.8, 22.3 and 22.6°.

3. The compound of the formula (II) according to claim 1, in crystalline form of modification 1, characterized in that the IR spectrum of the compound has band maxima at 3381, 1691, 1565, 1524 and 1419 cm-1.

4. A method for preparing the compound of the formula (II) of claim 1 in crystalline modification 1 comprising dissolving a compound of the formula (I)

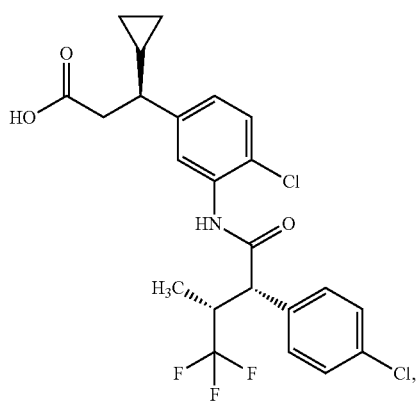

in a polar aprotic solvent, adding a base selected from the group consisting of sodium hydroxide and a sterically demanding sodium alkoxide, stirring, filtering to obtain a solid, isolating and drying.

5. The method of claim 4, wherein the polar aprotic solvent used is acetonitrile and the base used is sodium hydroxide in solid form.

6. The method of claim 4, wherein the solvent used is acetonitrile and the base used is sodium tert-butoxide or sodium 2-methylbut-2-oxide.

7. The method of claim 4, wherein the base is added in an amount of 0.7 to 1.0 molar equivalents, based on the compound of the formula (I).

8. A medicament comprising the compound of claim 1 in combination with one or more other active ingredients selected from the group consisting of organic nitrates, NO donors, cGMP-PDE inhibitors, stimulators of guanylate cyclase, antithrombotics, antihypertensive agents, MR antagonists, IP receptor agonists, compounds having anti-inflammatory action, antidementives, antidiabetics, active compounds which modify fat metabolism and active compounds for the treatment of bone and muscle disorders.

9. Osmotic release system consisting of a core and a shell, where the shell consists of a water-permeable material impermeable for the components of the core and has at least one orifice, and where the core comprises sodium (3S)-3-(4-chloro-3-{[(2S,3R)-2-(4-chlorophenyl)-4,4,4-trifluoro-3-methylbutanoyl]amino}phenyl)-3-cyclopropylpropanoate of the formula (II)

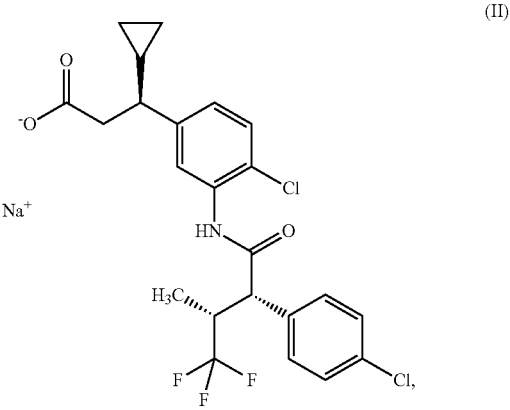

and at least one hydrophilic swellable polymer.

10. Osmotic release system according to claim 9, where the core of the osmotic release system comprises
　　0.5% by weight to 50% by weight of the compound of the formula (II),
　　40% by weight to 99.5% by weight of at least one hydrophilic swellable polymer
and optionally at least one osmotically active additive and optionally at least one pharmaceutically customary auxiliary.

11. Osmotic release system according to claim 9, where the core comprises a two-chamber system consisting of an active ingredient layer and an osmosis layer.

12. Osmotic release system according to claim 11, where the active ingredient layer comprises
　　1% by weight to 50% by weight of the compound of the formula (II),
　　20% by weight to 99% by weight of at least one hydrophilic swellable polymer,
optionally at least one osmotically active additive and optionally at least one pharmaceutically customary auxiliary and the osmosis layer comprises
　　40% by weight to 90% by weight of at least one hydrophilic swellable polymer,
　　10% by weight to 60% by weight of an osmotically active additive and optionally at least one pharmaceutically customary auxiliary.

13. Osmotic release system according to claim 9, where the at least one hydrophilic swellable polymer is selected from the group consisting of polyethylene oxide, xanthan, hydroxypropylcellulose, hydroxypropylmethyl cellulose, sodium carboxymethylcellulose, sodium carboxymethyl starch, vinylpyrrolidone/vinyl acetate copolymer and polyacrylic acids.

14. Osmotic release system according to claim 9, where the at least one hydrophilic swellable polymer is polyethylene oxide.

15. Osmotic release system according to claim 12, where the at least one hydrophilic swellable polymer of the active ingredient layer is polyethylene oxide having a viscosity of 40 to 100 mPa·s (measured in a 5% strength aqueous solution, 25° C.) and the at least one hydrophilic swellable polymer of the osmosis layer is polyethylene oxide having a viscosity of 5000 to 8000 mPa·s (measured in a 1% strength aqueous solution, 25° C.).

16. Osmotic release system according to claim 9, where the shell consists of cellulose acetate or a mixture of cellulose acetate and polyethylene glycol.

17. A process for preparing the osmotic release system of claim 9, comprising mixing sodium (3 S)-3-(4-chloro-3-{[(2S,3R)-2-(4-chlorophenyl)-4,4,4-trifluoro-3-methylbutanoyl]amino}phenyl)-3-cyclopropylpropanoate of the formula (II) and the at least one hydrophilic swellable polymer together to form a resulting mixture, granulating the resulting mixture, tableting to form a resulting core, coating the resulting core with the shell, and providing the shell the shell with one or more orifices suitable for the compound of the formula (II) exiting.

18. A process for preparing the osmotic release system of claim 11 in which the osmosis layer has components, comprising
mixing sodium (3 S)-3-(4-chloro-3-{[(2S,3R)-2-(4-chlorophenyl)-4,4,4-trifluoro-3-methylbutanoyl]amino}phenyl)-3-cyclopropylpropanoate of the formula (II) and the at least one hydrophilic swellable polymer of the active ingredient layer together to form a resulting mixture,
granulating the resulting mixture to form a set of active layer granules,
mixing the components of the osmosis layer to form a resulting osmosis layer mixture,
granulating the resulting osmosis layer mixture to form a set of osmosis layer granules,
compressing the set of active layer granules and the set of osmosis layer granules on a bilayer tablet press to give a bilayer tablet,
coating the bilayer tablet with the shell and
providing the shell, on the active ingredient side, with one or more orifices.

19. A method for the treatment and/or prevention of one or more diseases and disorders selected from the group consisting of renal and cardiorenal disorders, cardiac and cardiovascular disorders, pulmonary and cardiopulmonary disorders, disorders of the central nervous system, bone disorders, thromboembolic disorders, muscular dystrophies, ischaemias, vascular disorders, impaired microcirculation, fibrotic disorders, inflammatory disorders, and metabolic disorders, in humans and animals comprising administering an effective amount of the compound of claim 1 to a human or animal in need thereof.

20. The method of claim 19, wherein the renal and cardiorenal disorders are selected from the group consisting of chronic kidney disease (CKD) and diabetic kidney disease (DKD), the cardiac and cardiovascular disorders are selected from the group consisting of heart failure (HFpEF and HFrEF), myocardial infarction, angina pectoris, cardiomyopathies, hypertension and arteriosclerosis, the pulmonary and cardiopulmonary disorder is pulmonary hypertension (PH), the disorders of the central nervous system is dementia, the bone disorders is osteogenesis imperfect, the fibrotic disorders is systemic sclerosis, and the metabolic disorder is selected from the group consisting of metabolic syndrome, dyslipidaemia and diabetes.

21. The method of claim 19, wherein the compound of claim 1 is in crystalline form of modification 1 characterized in that the X-ray diffractogram of the compound has peak maxima of the 2 theta angle at 8.1, 17.2, 18.8, 22.3 and 22.6°.

22. A method for the treatment and/or prevention of one or more diseases and disorders selected from the group consisting of renal and cardiorenal disorders, cardiac and cardiovascular disorders, pulmonary and cardiopulmonary disorders, disorders of the central nervous system, bone disorders, thromboembolic disorders, muscular dystrophies, ischaemias, vascular disorders, impaired microcirculation, fibrotic disorders, inflammatory disorders, and metabolic disorders in humans and animals comprising administering an effective amount of the osmotic release system of claim 9 to a human or animal in need thereof.

23. The method of claim 22, wherein the renal and cardiorenal disorders are selected from the group consisting of chronic kidney disease (CKD) and diabetic kidney disease (DKD), the cardiac and cardiovascular disorders are selected from the group consisting of heart failure (HFpEF and HFrEF), myocardial infarction, angina pectoris, cardiomyopathies, hypertension and arteriosclerosis, the pulmonary and cardiopulmonary disorder is pulmonary hypertension (PH), the disorders of the central nervous system is, dementia, the bone disorders is osteogenesis imperfect, the fibrotic disorders is systemic sclerosis, and the metabolic disorder is selected from the group consisting of metabolic syndrome, dyslipidaemia and diabetes.

24. A method for the treatment and/or prevention of one or more diseases and disorders selected from the group consisting of renal and cardiorenal disorders, cardiac and cardiovascular disorders, pulmonary and cardiopulmonary disorders, disorders of the central nervous system, bone disorders, thromboembolic disorders, muscular dystrophies, ischaemias, vascular disorders, impaired microcirculation, fibrotic disorders, inflammatory disorders, and metabolic disorders in humans and animals comprising administering an effective amount of the osmotic release system of claim 11 to a human or animal in need thereof.

25. A method for the treatment and/or prevention of one or more diseases and disorders selected from the group consisting of renal and cardiorenal disorders, cardiac and cardiovascular disorders, pulmonary and cardiopulmonary disorders, disorders of the central nervous system, bone disorders, thromboembolic disorders, muscular dystrophies, ischaemias, vascular disorders, impaired microcirculation, fibrotic disorders, inflammatory disorders, and metabolic disorders in humans and animals comprising administering an effective amount of the osmotic release system of claim 12 to a human or animal in need thereof.

* * * * *

UNITED STATES PATENT AND TRADEMARK OFFICE
CERTIFICATE OF CORRECTION

PATENT NO. : 10,905,667 B2
APPLICATION NO. : 16/043567
DATED : February 2, 2021
INVENTOR(S) : Anke Stroyer et al.

Page 1 of 1

It is certified that error appears in the above-identified patent and that said Letters Patent is hereby corrected as shown below:

In the Specification

Column 22, Line 3, "3 cells" should be --β cells--.

Column 37, Line 31 "1.8 rpm" should be --1.8 μm--.

Column 37, Line 58, "5 m" should be --5 μm--.

In the Claims

Column 45, Claim 17, Line 27, "providing the shell the shell with" should be --providing the shell with--.

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*